(12) United States Patent
Saito et al.

(10) Patent No.: US 9,452,621 B2
(45) Date of Patent: Sep. 27, 2016

(54) INK JET PRINTING APPARATUS AND METHOD FOR ESTIMATING MOISTURE CONTENT OF PRINT SHEET

(71) Applicant: CANON KABUSHIKI KAISHA, Tokyo (JP)

(72) Inventors: Riichi Saito, Fujisawa (JP); Noboru Toyama, Kawasaki (JP); Takaharu Aotani, Tokyo (JP)

(73) Assignee: Canon Kabushiki Kaisha, Tokyo (JP)

( * ) Notice: Subject to any disclaimer, the term of this patent is extended or adjusted under 35 U.S.C. 154(b) by 0 days.

(21) Appl. No.: 14/692,084

(22) Filed: Apr. 21, 2015

(65) Prior Publication Data

US 2015/0298470 A1    Oct. 22, 2015

Related U.S. Application Data

(62) Division of application No. 14/287,754, filed on May 27, 2014, now Pat. No. 9,038,444.

(30) Foreign Application Priority Data

Jun. 4, 2013 (JP) .................................. 2013-118029

(51) Int. Cl.
*B41J 11/00* (2006.01)
*G01N 19/10* (2006.01)

(52) U.S. Cl.
CPC ........... *B41J 11/0095* (2013.01); *B41J 11/002* (2013.01); *B41J 11/0005* (2013.01); *G01N 19/10* (2013.01)

(58) Field of Classification Search
CPC .................................................. B41J 11/0085
See application file for complete search history.

(56) References Cited

U.S. PATENT DOCUMENTS

| | | | |
|---|---|---|---|
| 3,345,441 A | 10/1967 | Dibdin | |
| 3,613,437 A | 10/1971 | Colgren et al. | |
| 4,655,076 A | 4/1987 | Weihe et al. | |
| 2003/0038420 A1* | 2/2003 | Cleary | B41J 11/007 271/197 |

(Continued)

FOREIGN PATENT DOCUMENTS

| | | | |
|---|---|---|---|
| JP | 07-234556 A | | 9/1995 |
| JP | 2001239715 A | * | 9/2001 |

(Continued)

OTHER PUBLICATIONS

Machine generated English translation of JP 2001-239715A to Obata et al., "Label Printer and Apparatus for Producing Label"; generated via https://www4.j-platpat.inpit.go.jp/cgi-bin/tran_web_cgi_ejje?u=http://www4.j-platpat.inpit.go.jp/eng/translation/20160116053617032265895134628577288 1AEE4D84AD9A1B-FB715B490E6FBE87F on Jan. 15, 2016.*

*Primary Examiner* — Shelby Fidler
(74) *Attorney, Agent, or Firm* — Fitzpatrick, Cella, Harper & Scinto

(57) ABSTRACT

In an ink jet printing apparatus, a moisture content of a print sheet is estimated without decreasing productivity of the printing apparatus and appropriate conditions of printing operation in the subsequent printing process are specified. More specifically, by measuring a change in thickness of the print sheet after printing, a state of moisture content is estimated. Estimating a state of moisture content allows determination of appropriate conditions of the printing operation such as a minimum drying time required for printing a high-quality image on various types of print sheets such as print coated paper or coated paper.

7 Claims, 30 Drawing Sheets

(56) References Cited

U.S. PATENT DOCUMENTS

2010/0171782 A1* 7/2010 Kado .................. B41J 11/0005
    347/16

FOREIGN PATENT DOCUMENTS

| JP | 2011-051215 A | 3/2011 |
| JP | 2012-183798 A | 9/2012 |

* cited by examiner

FRONT VIEW

TOP VIEW

| INK EJECTION AMOUNT | 4g/m² | 7g/m² | 14g/m² | 21g/m² | 28g/m² |
|---|---|---|---|---|---|
| DECREASING CHANGE RATE: α | -0.5 | -1.0 | -1.2 | -2.0 | -3.5 |
| COCKLING DETERMINATION | ○ | ○ | △ | × | × |

FIG.25

| DRYING CONDITION | a1 | a2 | a3 | a4 | a5 |
|---|---|---|---|---|---|
| DRYING TEMPERATURE | ROOM TEMPERATURE | 50°C | 70°C | 90°C | 110°C |
| DECREASING CHANGE RATE: α | −3.5 | −2.0 | −1.0 | −0.5 | 0.0 |

FIG.26

| DRYING CONDITION | b1 | b2 | b3 | b4 |
|---|---|---|---|---|
| TEMPERATURE IMMEDIATELY ABOVE PRINT MEDIUM | ROOM TEMPERATURE | 50°C | 70°C | 90°C |
| DECREASING CHANGE RATE: α | -2.0 | -1.5 | -1.0 | -0.2 |

FIG.28

| SUCTION CONDITION | a1 | a2 | a3 | a4 | a5 |
|---|---|---|---|---|---|
| SUCTION FORCE | 0 | -10kPa | -30kPa | -50kPa | -70kPa |
| DECREASING CHANGE RATE | × MEASUREMENT FAILED DUE TO DEFORMATION | -2.0 | -1.5 | -1.0 | -0.5 |

FIG.30

INK JET PRINTING APPARATUS AND METHOD FOR ESTIMATING MOISTURE CONTENT OF PRINT SHEET

BACKGROUND OF THE INVENTION

1. Field of the Invention

The present invention relates to an ink jet printing apparatus and a method for estimating a moisture content of a print sheet. More specifically, the present invention relates to the technique of estimating a moisture content of ink ejected to a print sheet by ink jet printing and reducing deformation (curling or cockling) of the print sheet based on the estimation.

2. Description of the Related Art

Such deformation of print sheets is noticeable in the case of performing high-speed printing to a print sheet that is not a special sheet for ink jet printing, such as commercial offset printing paper, by using aqueous ink. Generally, paper used for the print sheets has properties of expanding when fibers in the paper swell with the paper containing moisture and shrinking when fibers shrink with the paper being dried. This causes curling or cockling of the print sheets due to moisture of ink when ejected to the print sheets.

To solve the above problem, Japanese Patent Laid-open No. 2012-183798 discloses the technique of controlling ejection of ink and drying of ink based on a moisture content measured by an infrared moisture gauge, thereby reducing deformation of print sheets immediately after ink jet printing. Furthermore, Japanese Patent Laid-open No. 2011-51215 discloses, based on the relationship between a moisture content of a print sheet and a change in size of the print sheet, drying the print sheet so that the difference in moisture content between an image portion and a non-image portion of the print sheet immediately before a paper discharging step becomes equal to or smaller than 3.0 g/m² to reduce cockling. Here, the moisture content is measured by a known method such as a Karl Fischer apparatus.

However, the techniques disclosed in Japanese Patent Laid-open Nos. 2012-183798 and 2011-51215 have a problem that operations and mechanisms for obtaining a moisture content of the print sheet are complicated in the first place, and as a result, productivity of the printing apparatus decreases.

More specifically, the infrared moisture gauge disclosed in Japanese Patent Laid-open No. 2012-183798 requires an operation or processing for obtaining a calibration curve between the reflection intensity of near-infrared rays (IM-D value) and the moisture content for each of color material and concentration of ink used for printing, temperature of a print sheet, and the like. Accordingly, when a new type of print sheet or ink is used, it is necessary to create a calibration curve for each drying temperature, and as a result, productivity of the printing apparatus decreases. Meanwhile, in a case where a trace moisture gauge employing a microwave resonator is used, unlike the method using infrared rays, it is possible to measure a color print sheet without the influence of heat. However, since measurement is made on a dielectric loss factor of water when microwaves pass through the print sheet, it is not easy to measure the dielectric loss factor in a state in which microwaves are passing through the print sheet during a printing operation in which the print sheet is fixed to a sheet holding member, such as a stage, belt, or drum.

On the other hand, the Karl Fischer apparatus or the like using a measurement sample as disclosed in Japanese Patent Laid-open No. 2011-51215 requires creating a sample for each drying temperature when using a new print sheet or ink, and as a result, productivity may decrease.

SUMMARY OF THE INVENTION

An object of the present invention is to provide a method and an ink jet printing apparatus for estimating a moisture content of a print sheet without decreasing productivity.

In a first aspect of the present invention, there is provided a printing apparatus comprising: a printing unit configured to perform printing by applying ink to a sheet; a measuring unit configured to measure a thickness of a sheet to which ink has been applied; and a determination unit configured to determine an operating condition in printing performed by said printing unit, based on the measured thickness.

In a second aspect of the present invention, there is provided a printing method comprising the steps of: measuring a thickness of a sheet to which liquid has been applied; and determining an operating condition in printing in which ink is applied to a sheet, based on the measured thickness.

In a third aspect of the present invention, there is provided a method of estimating moisture content, the method comprising the steps of: measuring a thickness of a medium to which liquid has been applied; and estimating moisture content of the medium based on a change rate of the thickness of the medium.

According to the above structures, the ink jet printing apparatus makes it possible to estimate a moisture content of a print sheet without decreasing productivity of the apparatus and to specify appropriate conditions of printing operation in the subsequent printing process.

Further features of the present invention will become apparent from the following description of exemplary embodiments (with reference to the attached drawings).

BRIEF DESCRIPTION OF THE DRAWINGS

FIG. 25 shows a thickness decreasing change rate $\alpha$ and a determination result of cockling by a visual check of the print sheet for each ejection amount according to the sixth example;

FIG. 26 shows the relationship between a temperature of the print sheet (drying condition) and the thickness decreasing change rate $\alpha$ according to the sixth example;

FIG. 28 shows the relationship between a temperature of airflow immediately above the print sheet (drying condition) and the thickness decreasing change rate $\alpha$ according to the seventh example;

FIG. 30 shows the relationship between a temperature of the print sheet (drying condition) and the thickness decreasing change rate $\alpha$ according to the eighth example.

DESCRIPTION OF THE EMBODIMENTS

Embodiments of the present invention will be described below in detail with reference to the drawings.

Figure 1A:
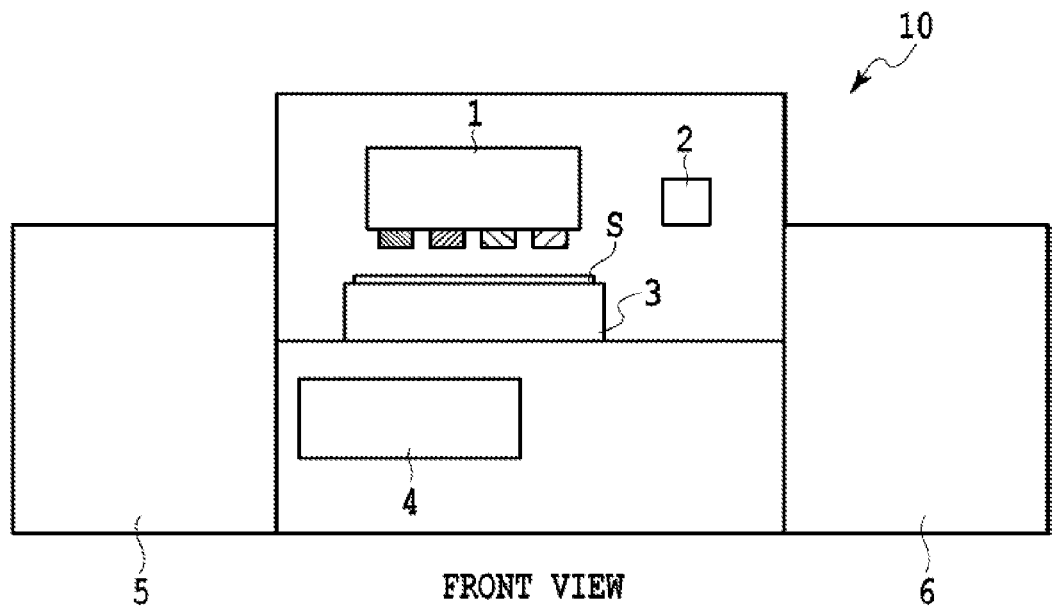
FIG. 1A and FIG. 1B are a front view and a top view of a schematic diagram of a printing apparatus 10, respectively, according to one embodiment of the present invention.
Figure 1B:
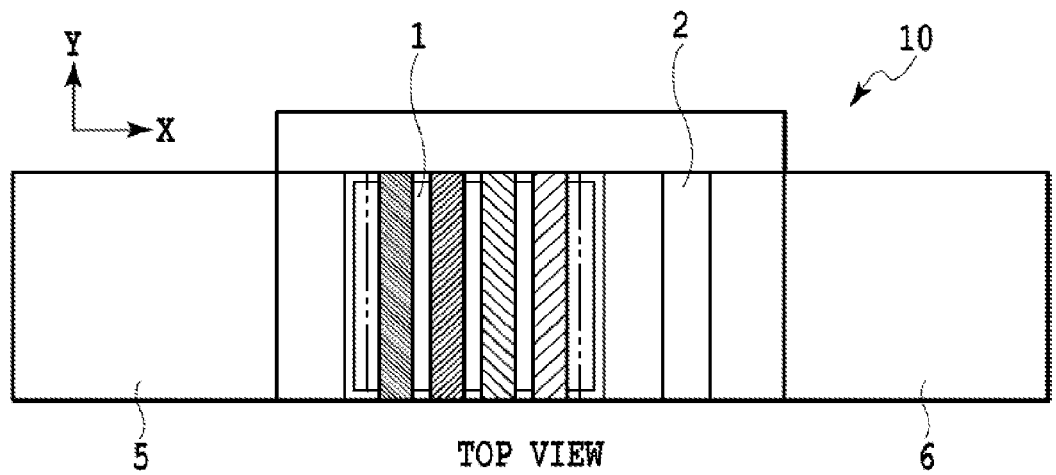

FIG. 1A and FIG. 1B are a front view and a top view of a schematic diagram of a printing apparatus 10, respectively, according to one embodiment of the present invention. As shown in FIG. 1A and FIG. 1B, the ink jet printing apparatus 10 is composed by using an ink-jet printing part 1, a thickness measuring part 2 for measuring a thickness of a print sheet which is conveyed, a sheet conveying part 3, and a control part 4. The printing apparatus 10 further includes a sheet supply part 5 for supplying print sheets to the printing part 1, and a sheet discharge part 6 for discharging the print sheets on which printing has been performed. The printing part 1 applies ink (liquid) ejected from a print head (ink jet head) to the print sheet (hereinafter also referred to simply as a "sheet" or "print medium") conveyed along the X axis in a left-to-right direction to print an image, as shown in FIGS. 1A and 1B. The print head of the present embodiment is a line-type print head in which nozzles for ejecting ink are arranged across an area corresponding to a maximum width of a sheet assumed to be used. In a sheet movement direction (conveying direction), there are provided four print heads corresponding to four colors of ink: cyan, magenta, yellow, and black. Of course, the number of ink colors and the number of print heads are not limited to four. In addition, any ink jet systems, such as a system using a heat generating element, a system using a piezoelectric element, and a system using an electrostatic element, can be used. Each color ink is supplied individually to the print head from an ink tank (not shown) via an ink tube (not shown).

The control part 4 has a controller having a CPU, memory, and various I/O interfaces, and a user interface consisting of an input unit for a user to input and output various kinds of information and a display. Operation and processing in the apparatus of the present invention are controlled by the controller in the control part 4 or controlled based on instructions from an external device such as a host computer connected to the controller via I/O interfaces.

Figure 2A:
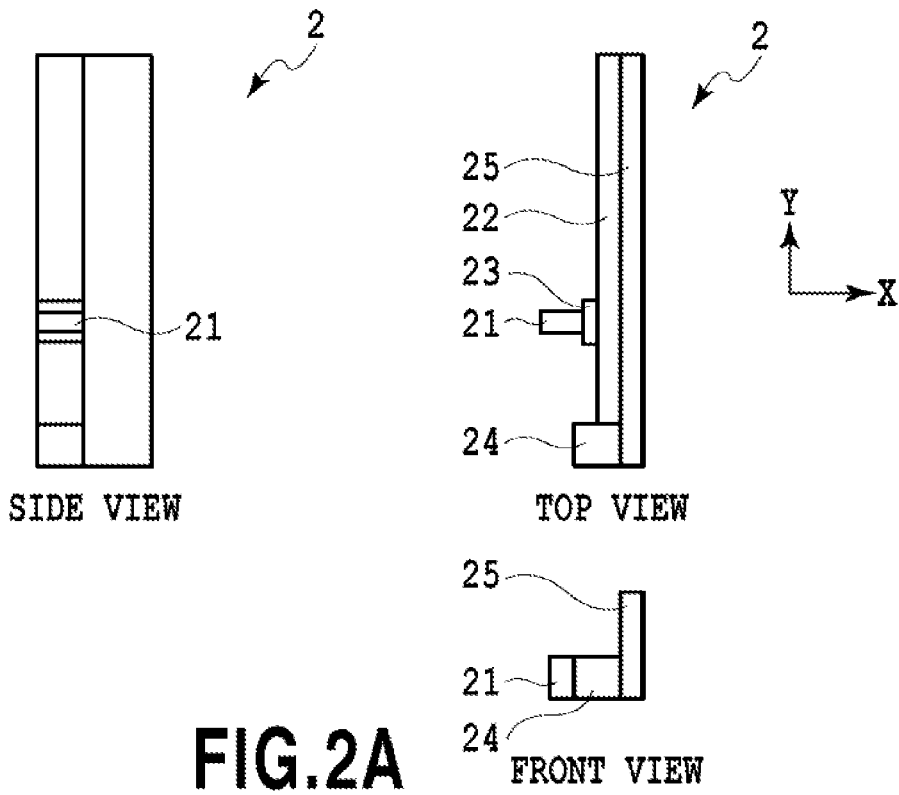
FIG. 2A and FIG. 2B show two modes of a detailed structure of a thickness measuring part 2 of FIG. 1A and FIG. 1B.
Figure 2B:
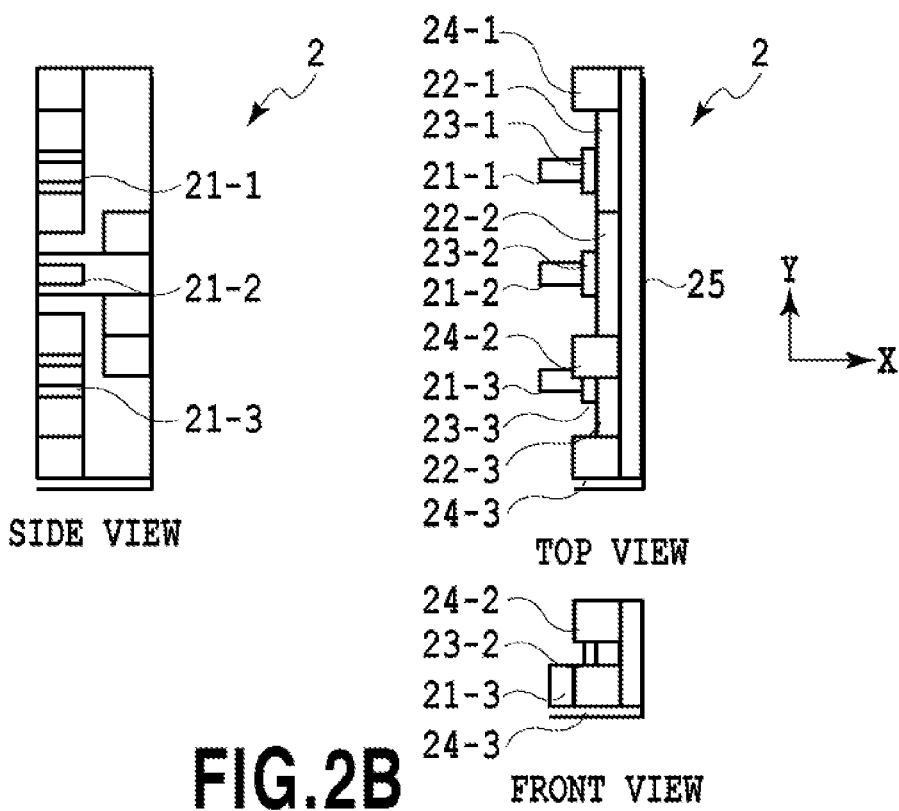

FIG. 2A and FIG. 2B show two modes of a detailed structure of the thickness measuring part 2 of FIG. 1A and FIG. 1B. Measurement systems of the thickness measuring part 2 are roughly divided into two types: a contact type such as magnetic measurement system and a noncontact type such as a laser length measuring system. The noncontact type is preferable since there is a concern about adhesion of ink. More specifically, in the laser length measuring system, the distance between a sensor and a surface of the sheet conveying part 3 which tightly holds the back side of the sheet is set to zero in advance, and the distance from the sensor to the front side of the printed sheet from the sensor is measured. The difference in distance is indirectly considered to be a thickness.

As shown in FIG. 2A, in the thickness measuring part 2, the control part 4 controls a length measuring sensor 21 of the laser length measuring system to move along the Y axis in the top view of FIG. 2A. More specifically, the length measuring sensor 21 is connected to a guide rail 22 provided on a frame 25 via a base 23, and a driving force of a driving motor 24 is transmitted to the length measuring sensor 21 so as to move along the Y axis. Meanwhile, the printed sheet can move along the X axis by the sheet conveying part 3 as will be described later with reference to FIG. 3A and FIG. 3B. These movements allow measurement of a change in distance in a thickness direction of a print sheet at specified coordinates (x, y), and the result can be stored in memory (not shown).

In the other mode shown in FIG. 2B, it is also possible to measure changes in distance at a plurality of points at the same time by using a plurality of length measuring sensors. As shown by the example using three sensors in FIG. 2B, a length measuring sensor 21-1, a length measuring sensor 21-2, and a length measuring sensor 21-3 are arranged along the Y axis in the top view of FIG. 2B. These length measuring sensors 21-1, 21-2, and 21-3 are connected to guide rails 22-1, 22-2, and 22-3 via bases 23-1, 23-2, and 23-3, respectively. Under the control of the control part 4, the driving forces of driving motors 24-1, 24-2, and 24-3 allow the length measuring sensors 21-1, 21-2, and 21-3 to move along the Y axis, respectively. Meanwhile, the sheet conveying part 3 allows the printed sheet to move along the X axis. Accordingly, it is possible to measure changes in distance in a thickness direction of a sheet at the same time at specified coordinates (x, y1), (x, y2), and (x, y3), and the results can be stored in memory. In a case where the thickness measuring part 2 uses an array-type length measuring sensor having a resolution n in a range corresponding to a maximum width of a sheet assumed to be used, it is possible to measure changes in distance at coordinates (x, y1) to (x, yn) along the Y axis.

Figure 3A:
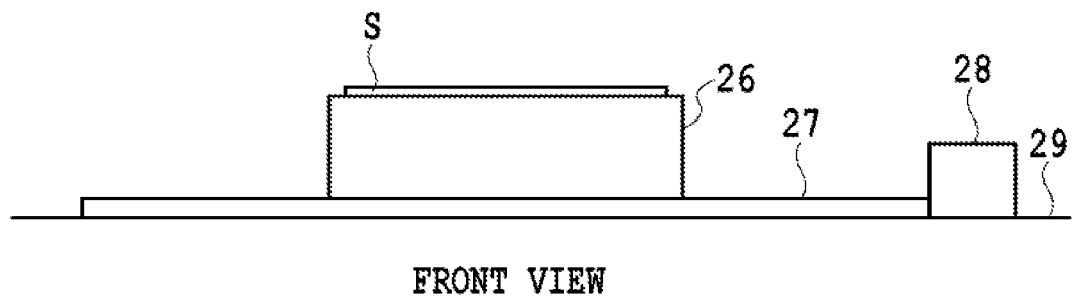
FIG. 3A and FIG. 3B are a front view and a top view of a detailed structure of a print sheet conveying part 3 of FIG. 1A and FIG. 1B, respectively.
Figure 3B:
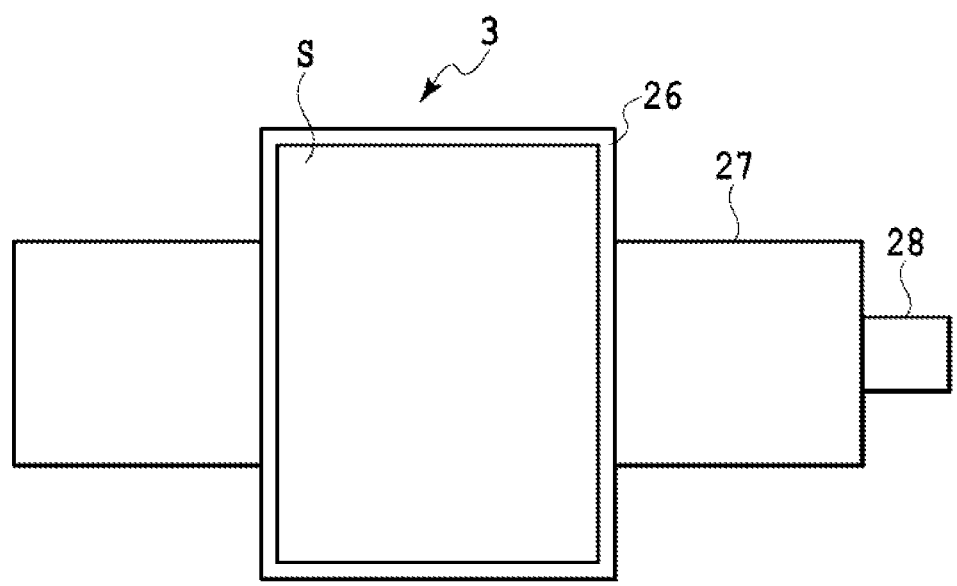

FIG. 3A and FIG. 3B are a front view and a top view of a detailed structure of the sheet conveying part 3 of FIG. 1A and FIG. 1B, respectively. The sheet conveying part 3 is a stage unit for conveying a print sheet to a specified position while holding the back side of the print sheet. A holding system may use a vacuum suction system, an electrostatic suction system, and the like. As shown in FIG. 3A and FIG. 3B, a stage 26 for holding a sheet S, a guide rail 27 for guiding a movement of the stage 26, and a driving motor 28 for generating a driving force for the movement are provided on a mount 29. By the control part 4 controlling the driving motor 28, the sheet conveying part 3 moves from the sheet supply part 5 at the left side of the printing apparatus 10 of FIGS. 1A and 1B, passing by the printing part 1 and the thickness measuring part 2, to the sheet discharge part 6 at the right side of the printing apparatus 10 of FIGS. 1A and 1B, along the guide rail 27. In this manner, since the sheet S is held by the stage 26 after printed through ink ejection, deformation of the sheet S is forcibly reduced, thereby preventing cockling or the like while the sheet S is held.

A description will be given of experiments in which the printing apparatus 10 of the present embodiment as described above is used to obtain a thickness change rate of a print sheet according to a moisture content of the print sheet through the ejection of ink.

Experiment 1

The present experiment uses the printing apparatus 10 and measures a thickness change rate of a print sheet when a pseudo ink not containing a color material component is ejected to a print sheet to form an image.

Figure 4A:
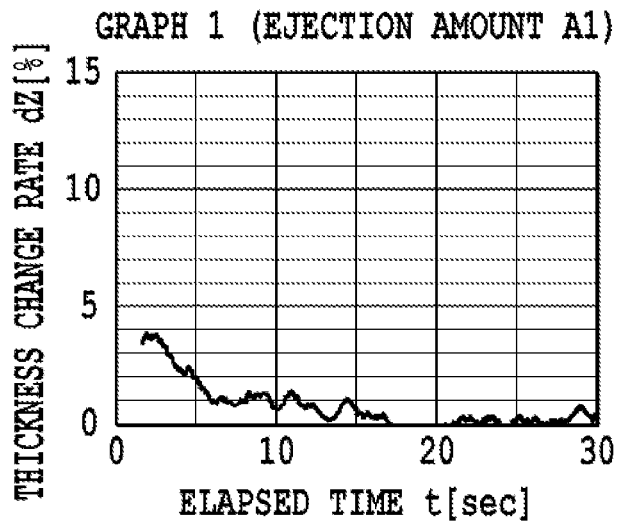
FIG. 4A to FIG. 4C are graphs showing the relationship between an elapsed time from printing and a thickness change rate of a print sheet when a pseudo ink A is ejected to the print sheet from a print head to form a given image.
Figure 4B:
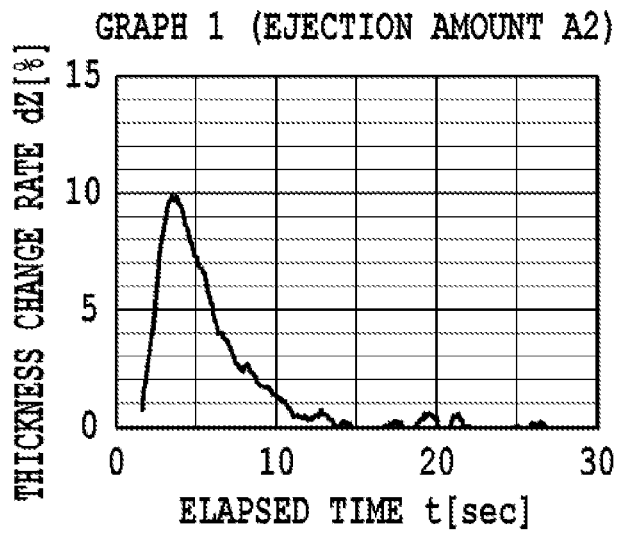
Figure 4C:
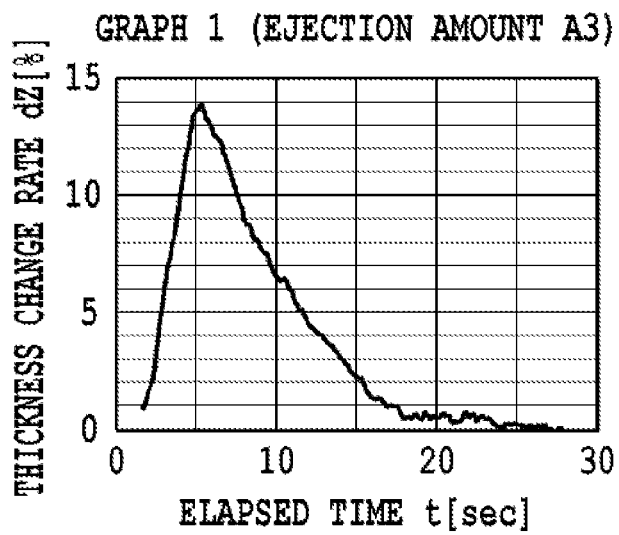

FIG. 4A to FIG. 4C are graphs showing the relationship between an elapsed time from printing and a thickness change rate of a print sheet when the pseudo ink A is ejected to the print sheet from a print head to form a given image. More specifically, in FIGS. 4A to 4C, ejection amounts from the print head are represented by A1, A2, and A3 (A1<A2<A3), and a thickness of a sheet in an image portion printed in the respective ejection amounts is measured by a laser. The results are shown with an elapsed time. In the laser length measuring, the distance between a sensor and a surface of the stage 26 of the sheet conveying part 3 which holds the back side of the sheet is set to zero in advance, and the distance from the sensor to the front side of the printed sheet is measured. The thickness is indirectly measured.

Figure 5A:
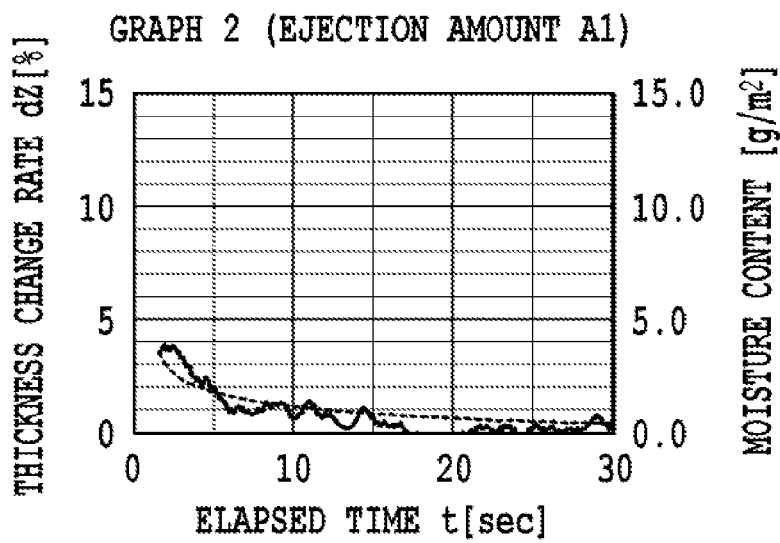
FIG. 5A to FIG. 5C are graphs showing comparison of the change in thickness of the print sheet shown in FIG. 4A to FIG. 4C with the change in moisture content of the print sheet.
Figure 5B:
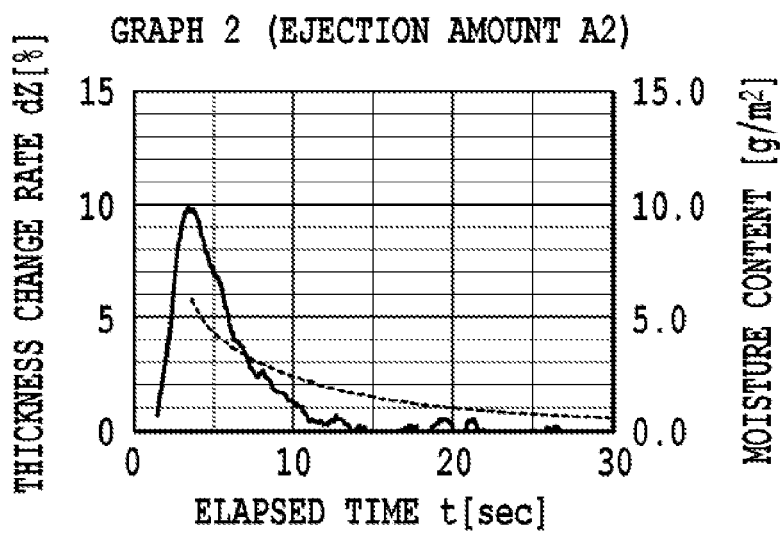
Figure 5C:
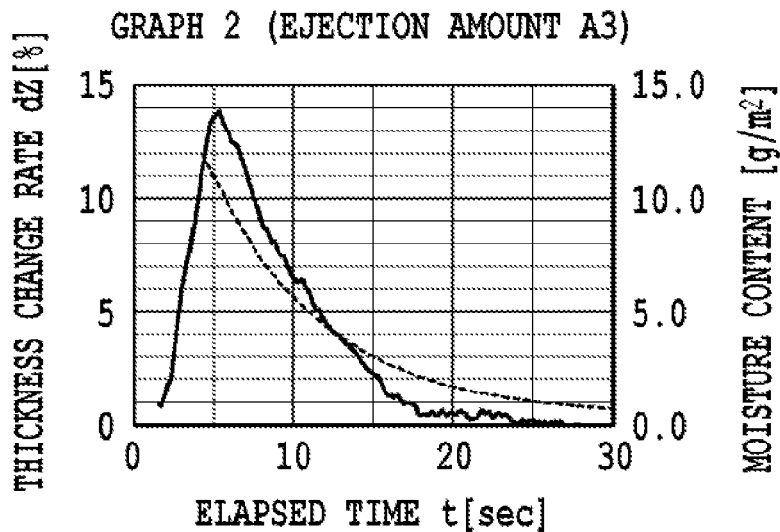

FIG. 5A to FIG. 5C are graphs showing comparison of a thickness change rate of a print sheet shown in FIGS. 4A to 4C with a change in moisture content of the print sheet. More specifically, FIGS. 5A to 5C show a moisture content of a sheet in an image portion printed in the ejection amounts A1, A2, and A3 with an elapsed time, along with a change in thickness of the sheet shown in FIGS. 4A to 4C. The change in moisture content over time is shown as a result of converting the reflection intensity (IM-D value) of the given image measured by an infrared moisture gauge into the moisture content based on a prepared calibration curve between the reflection intensity (IM-D value) and the moisture content. Here, the ink A is, as described, a pseudo ink not containing a color material component. Using the ink A can facilitate creation of a calibration curve by the infrared moisture gauge.

Figure 6:
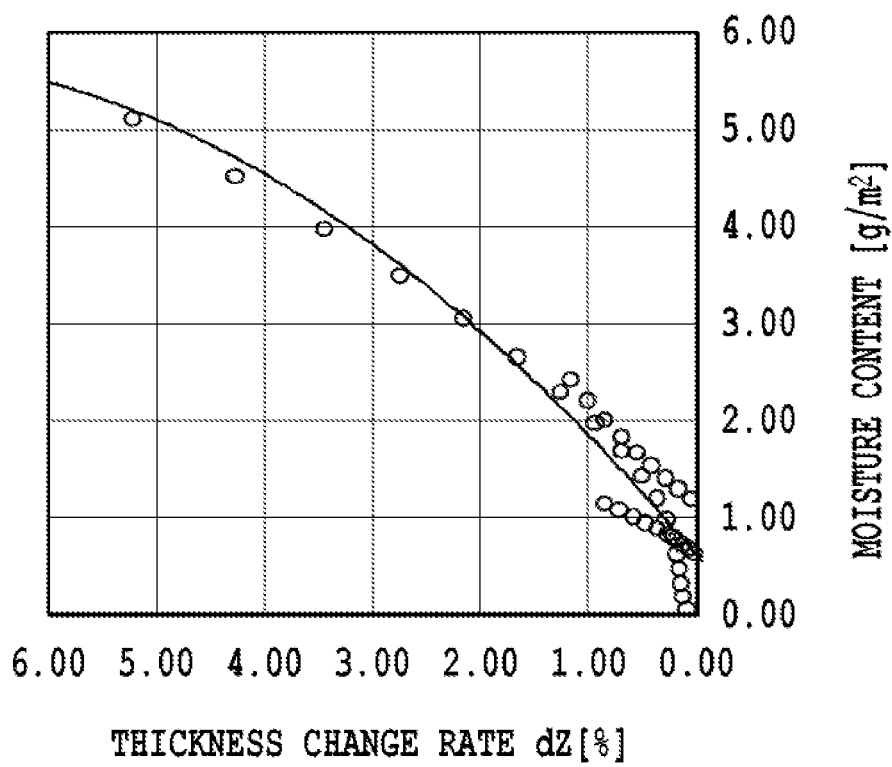
FIG. 6 is a graph showing the relationship between the change in thickness of the print sheet obtained from the relationship shown in FIG. 4A to FIG. 4C and the relationship shown in FIG. 5A to FIG. 5C and the change in moisture content of the print sheet.

FIG. 6 is a graph showing the relationship between the change in thickness of the print sheet obtained from the relationship shown in FIGS. 4A to 4C and the relationship shown in FIGS. 5A to 5C and the change in moisture content of the print sheet.

In the experiment to obtain the thickness and moisture content of a sheet shown in FIGS. 4A to 4C, FIGS. 5A to 5C, and FIG. 6, a print sheet B is heated to 70° C. and held by suction on the stage 26 of the sheet conveying part 3 at a suction pressure of −10 kPa. As described above, the ink A is a pseudo ink not containing a color material component to facilitate creation of a calibration curve by the infrared moisture gauge and contains 99% of pure water and 1% of others. The ejection amounts A1, A2, and A3 are 6 g/m$^2$, 13 g/m$^2$, and 19 g/m$^2$, respectively. The sheet conveying part 3 conveyed the print sheet B on which three types of images were printed to the thickness measuring part 2 and the thickness measuring part 2 measured the thicknesses of the three types of image portions on the sheet with an elapsed time. In the present experiment, measurements were made by three length measuring sensors of FIG. 2B for 60 seconds at the same time.

In FIGS. 4A to 4C and FIGS. 5A to 5C, the horizontal axis is an elapsed time t[sec] from printing at the printing part 1, the vertical axis is a thickness change rate dZ[%], and a solid line is the change in thickness change rate dZ[%] over time. In FIGS. 5A to 5C, a broken line is the change in moisture content dW over time. The thickness change rate dZ[%] is expressed by the following equation:

$$dZ[\%] = (Zt - Z^*)/Zo \times 100 \qquad (1).$$

Here, Zt is a thickness measurement value after an elapsed time t[sec] from printing, Z* is an average after 50 to 60 seconds after printing, and Zo is the thickness of the print sheet B. In the present experiment, New V Matt having a basis weight of 104.7 g/m$^2$ available from Mitsubishi Paper Mills Ltd. was used as the print sheet B. In this case, Zo is about 106 μm.

Regarding the change in thickness change rate dZ as shown in FIGS. 4A to 4C and FIGS. 5A to 5C, it is assumed that the thickness becomes the maximum since paper fibers temporarily expand immediately after printing, and then returns to the level before printing after the paper fibers shrink. When the ejection amounts satisfy A3>A2>A1, the maximum of the thickness change rate dZ tends to have a relation according to A3>A2>A1 and the time for the thickness to return to the level before printing tends to have a relation according to A3>A2>A1.

The moisture content $dW[g/m^2]$ is expressed by the following equation:

$$dW[g/m^2] = Wt - Wo \quad (2).$$

Here, Wt is a measurement value of the moisture content after an elapsed time t[sec] from printing and Wo is a measurement value of the moisture content immediately before printing.

Regarding the change in moisture content dW (broken line) shown in FIGS. 5A to 5C, the moisture content rapidly decreases immediately after printing, and gradually returns to the level before printing. When the ejection amounts satisfy A3>A2>A1, the maximum of the moisture content immediately after printing tends to have a relation according to A3>A2>A1 and the time for the moisture content to return to the level before printing tends to have a relation according to A3>A2>A1.

On the basis of the change in moisture content dW (broken line) and thickness change rate dZ (solid line) along with the elapsed time shown in FIGS. 5A to 5C, it is assumed that moisture of ink applied during printing penetrates into a base paper to destroy paper fibers (cellulose), and the printed portion swells to be a swollen state by water absorption and then to a dry and shrunk state in which the paper fibers are restructured due to a decrease in the moisture content by drying. In particular, a gradually descending curve of the moisture content $dW [g/m^2]$ as it returns to a level before printing and a gradually descending curve of the thickness change rate dZ [%] as it returns to a level before printing generally match in each of the ejection amounts A3, A2, and A1.

In particular, when the thickness change rate dZ is equal to or smaller than about 5%, it strongly correlates with the moisture content dW as shown in FIG. 6. The relationship of FIG. 6 is obtained by plotting pairs of a certain thickness change rate dZ and a moisture content dW after an elapsed time that is equal to the elapsed time to have the change rate dZ in FIGS. 5A to 5C, and then obtaining a quadratic curve based on the plots. The vertical axis of FIG. 6 is the moisture content $dW[g/m^2]$ and the horizontal axis is the thickness change rate dZ[%]. Based on the relationship shown in FIGS. 5A to 5C, the moisture content $dW[g/m^2]$ and the thickness change rate dZ[%] have the following relationship: as the thickness change rate dZ decreases from 5% to 1%, the moisture content $dW[g/m^2]$ tends to decrease generally along the quadratic curve. Therefore, in a case where an image is printed on the print sheet B with the ink A, based on the relationship shown by the quadratic curve of FIG. 6, it is assumed that the moisture content has the relationship with the thickness change rate as shown in the following Table 1.

TABLE 1

| Thickness change rate dZ[%] | 5.00 | 4.00 | 3.00 | 2.00 | 1.00 |
|---|---|---|---|---|---|
| Moisture content $dW[g/m^2]$ | 5.11 | 4.55 | 3.82 | 2.92 | 1.85 |

As described above, when an image is printed with a pseudo ink not containing a color material component by using the printing apparatus 10, the thickness change rate of the print sheet and the moisture content of the print sheet have the correlation, and under the conditions of the present experiment, the relationship as shown in Table 1 can be obtained.

Experiment 2

In the present experiment, the same experiment as the above-described Experiment 1 is performed by using a general ink containing a color material component to obtain the relationship of the moisture content with respect to the thickness change rate. More specifically, like Experiment 1, the present experiment measures a thickness of a print sheet in a given image printed by using the printing apparatus 10 shown in FIG. 1A to FIG. 3B and measures a moisture content to obtain the relationship of the moisture content with respect to the thickness change rate based on the measurements.

Figure 7A:
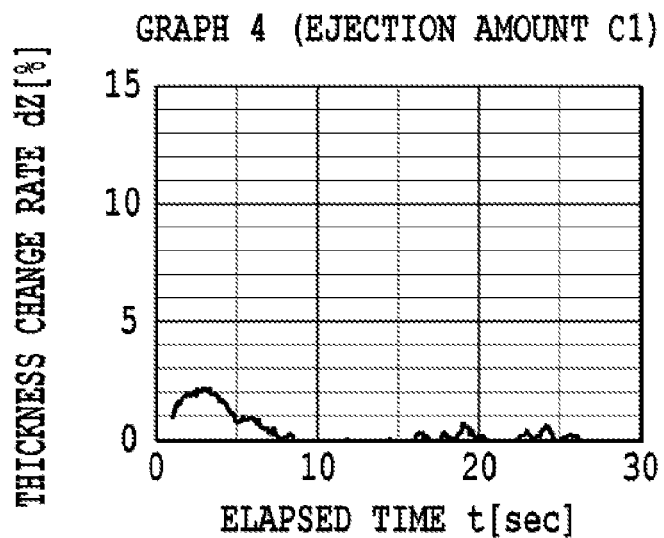
FIG. 7A to FIG. 7C are graphs showing the relationship between an elapsed time from printing and a thickness change rate of a print sheet when an ink C that is generally used in printing is ejected to the print sheet from a print head to form a given image.
Figure 7B:
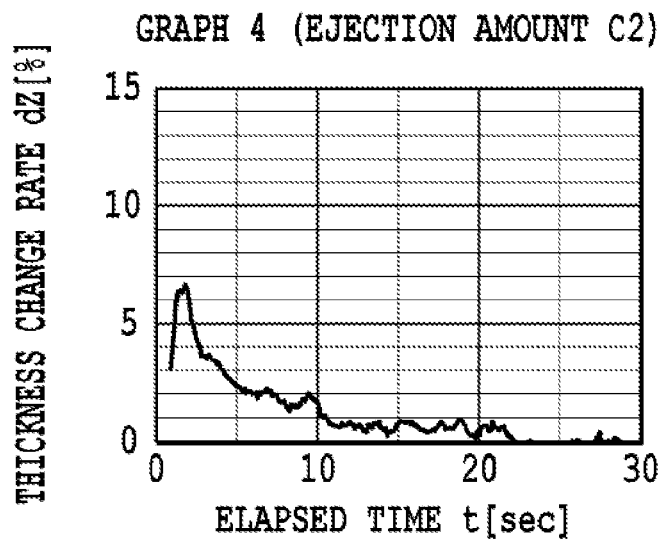
Figure 7C:
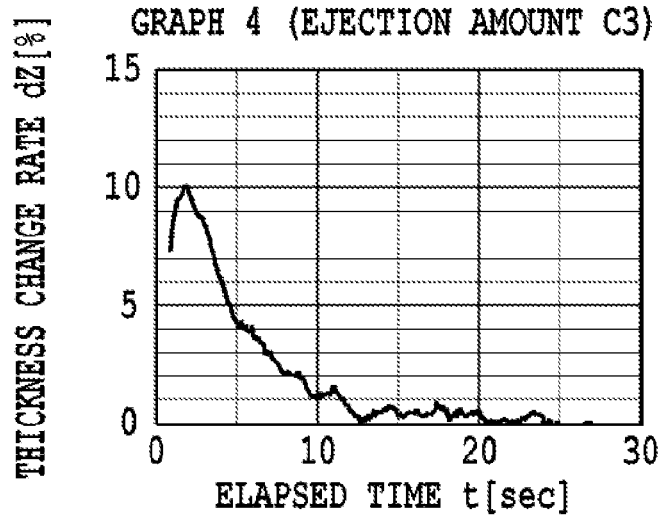
Figure 8A:
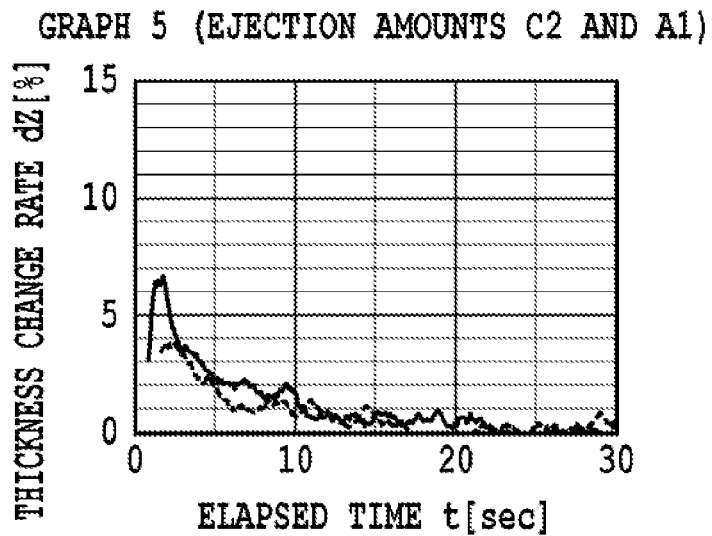
FIG. 8A and FIG. 8B are graphs respectively showing comparison of the thickness change rate shown in FIG. 7B and FIG. 7C with the thickness change rate obtained by an experiment according to an embodiment.
Figure 8B:
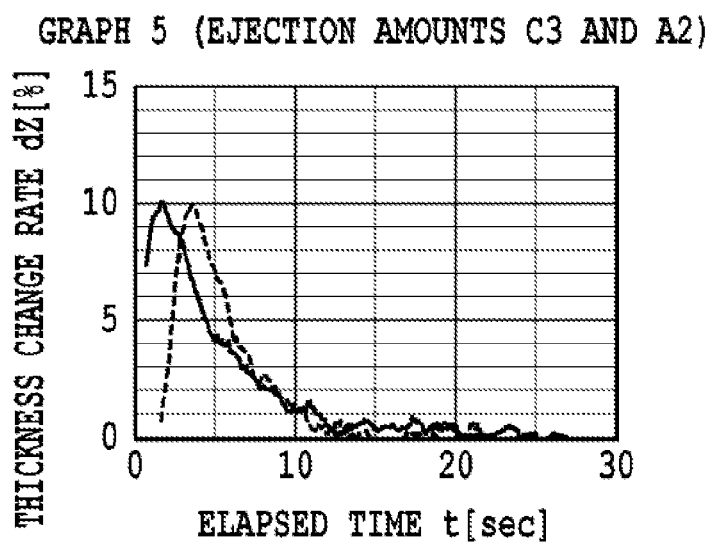

FIG. 7A to FIG. 7C are graphs showing the relationship between an elapsed time from printing and a thickness change rate of a print sheet when an ink C that is generally used in printing is ejected to the print sheet from a print head to form a given image. FIG. 8A and FIG. 8B are graphs respectively showing comparison of the thickness change rate (solid line) in the present experiment shown in FIG. 7B and FIG. 7C with the thickness change rate (broken line) in Experiment 1 shown in FIG. 4A and FIG. 4B. In FIG. 8A and FIG. 8B, the solid line and the broken line show similar movements of the thickness change rate.

In the present experiment, by using the printing apparatus 10, the ink C is ejected to a surface of a print sheet D held by the stage 26 of the sheet conveying part 3, and a thickness of an image portion printed in ejection amounts C1, C2, and C3 is measured by a laser with a lapse of time. FIGS. 7A to 7C show the change in thickness change rate with respect to an elapsed time based on the measurement results for each of the ejection amounts C1, C2, and C3. Here, the ink C is a general ink jet ink containing a color material component and contains 77% of pure water and 23% of others including a color material. The print sheet D is of the same type as the print sheet B used in Experiment 1.

In the present experiment, to the print sheet D heated to 70° C. and held by suction on the sheet conveying part 3 at a suction pressure of −10 kPa, the ink C is ejected from the print head in the ejection amounts C1, C2, and C3 to print three types of given images. The ejection amounts C1, C2, and C3 are 9 $g/m^2$, 18 $g/m^2$, and 28 $g/m^2$, respectively. Accordingly, amounts of water component in the ejection amounts C1, C2, and C3 are 7 $g/m^2$, 14 $g/m^2$, and 21 $g/m^2$, respectively.

The thickness measuring part 2 measures the thicknesses of three types of image portions on the sheet with a lapse of time. More specifically, the three images are measured at the same time for 60 seconds by using three length measuring sensors of FIG. 2B.

Regarding the change in thickness for each of the ejection amounts C1, C2, and C3 as shown in FIGS. 7A to 7C, it is assumed that the thickness becomes the maximum since paper fibers temporarily expand immediately after printing, and then returns to the level before printing after the paper fibers shrink. When the ejection amounts satisfy C3>C2>C1, the maximum of the thickness change rate dZ tends to have a relation according to C3>C2>C1. The time for the thickness to return to the level before printing is affected by a residue of the ink C, that is, 23% of others including a color material, and the time required for the thickness change rate dZ to be 2%, for example, tends to have a relation according to C3>C2>C1.

FIG. 8A and FIG. 8B respectively show the comparison results obtained by comparing the case of the ejection amount C2 (the moisture content is 14 g/m$^2$) with the case of the ejection amount A1 (6 g/m$^2$) and comparing the case of the ejection amount C3 (the moisture content is 21 g/m$^2$) with the case of the ejection amount A2 (13 g/m$^2$). Although the time required to reach the maximum of the thickness change rate dZ[%] slightly varies due to the difference in penetration speed or the like depending on the ink component, the graphs of ink C and ink A shown in each of figures have the same profile that shows a swollen state by water absorption followed by a dry and shrunk state. More specifically, like the ink A, it is confirmed that water component of the ink C penetrates into a base paper to destroy paper fibers (cellulose), and the printed portion swells to be a swollen state by water absorption and then to a dry and shrunk state in which the paper fibers are restructured due to a decrease in the moisture content by drying. Accordingly, as shown in FIG. 6, it is assumed that the moisture content dW[g/m$^2$] decreases as substantially a quadratic curve with respect to the decrease in the thickness change rate dZ by the ink C, and even in the case of using a general ink containing a color material component, the relationship shown in the aforementioned Table 1 is established.

As described above, in the case of using a general ink containing a color material component, like a pseudo ink not containing a color material component, the moisture content can be estimated from the thickness change rate dZ when an image is formed on a print sheet.

First Example

Figure 9:
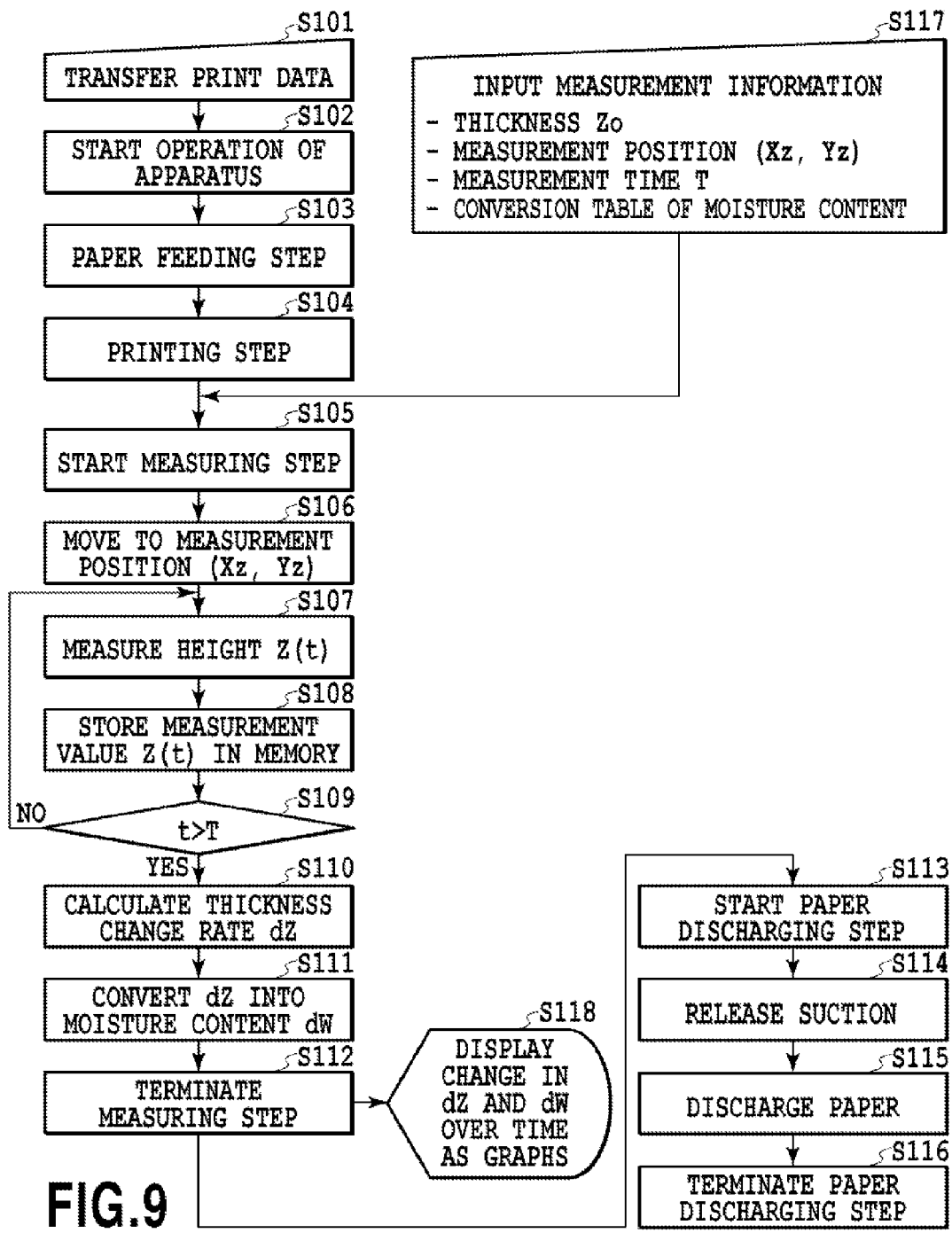
FIG. 9 is a flowchart of a process of estimating a moisture content according to one embodiment of the present invention.

A description will be given of a first example related to a method for estimating a moisture content of a print sheet from the change in thickness of the print sheet according to the above-described embodiment of the present invention. FIG. 9 is a flowchart of a process of estimating a moisture content. The process shown in FIG. 9 is performed in the printing apparatus 10 including the printing part 1, the thickness measuring part 2, the sheet conveying part 3, the control part 4, and others as described with reference to FIG. 1A and FIG. 1B. The process of the present example will be described according to the steps in the order mentioned in FIG. 9.

(S101 to S102: Print Data Transfer)

Print data is transferred by the controller in the control part 4 or an external device such as a host computer connected to the controller via I/O interfaces and is stored in memory. Then, the control and the processing in the printing apparatus are started.

(S103: Paper Feeding Step)

In the paper feeding step, a print sheet of the type based on the print data is fed. In the present example, a print sheet (New V Matt having a basis weight of 104.7 g/m$^2$ available from Mitsubishi Paper Mills Ltd.) is fed to the sheet conveying part 3, held by suction on the surface of the stage 26 which is heated to 70° C. at a suction pressure of −10 kPa, and conveyed to a printing area of the printing part 1.

(S104: Printing Step)

To the print sheet held by suction on the surface of the stage 26 at a suction pressure of −10 kPa and conveyed, ink is applied from a print head based on the print data, and a given image (test pattern) is printed for estimating a moisture content of the print sheet. In the present example, a rectangular pattern of 150 mm along the X axis direction and 10 mm along the Y axis direction is printed substantially in the center of an A5 sheet by using the above-mentioned ink C in an ejection amount of 28 g/m$^2$ (amount of water component of 21 g/m$^2$).

(S117: Input Measurement Information)

Measurement information is inputted from the controller in the control part 4 or an input device connected to the controller via I/O interfaces and is stored in memory. The measurement information includes four kinds of information: a thickness Zo of a print sheet, a position (Xz, Yz) on the print sheet at which thickness is measured, a measurement time T for which the thickness is measured, and a conversion table of a thickness change rate and a moisture content of the print sheet of interest measured in advance using a pseudo ink not containing a color material as described in the item of "Experiment 1" In the present example, the specific measurement information is:

Thickness Zo=106 μm (New V Matt having a basis weight of 104.7 g/m$^2$ available from Mitsubishi Paper Mills Ltd. (print sheet B));

Measurement position (Xz, Yz)=(105, 74), which is the center of A5 sheet given that the position of the print sheet corner is expressed as (0, 0);

Measurement time T=30 seconds; and

Conversion table of a thickness change rate and a moisture content=the above-described Table 1.

(S105 to S112, S118: Measuring Step)

The print sheet held by suction on the surface of the stage 26 at a suction pressure of −10 kPa is moved to the measurement position (Xz, Yz), and the change in height Z(t)[μm] is measured for the measurement time T at intervals of 0.1 second. Every measurement value is stored in memory. In the present example, the print sheet is moved to the measurement position (105, 74) and the change in height Z(t)[μm] is measured for 30 seconds at intervals of 0.1 second. Every measurement value is stored in memory. After the measurement, the thickness change rate dZ(t)[%] for each measurement time is obtained by the following equation (S110):

$$dZ(t)[\%]=(Z(t)-Zo)/Zo\times 100 \quad (3)$$

Here, Z(t) is a measurement value after an elapsed time t[sec] from printing, and Zo is a thickness of the print sheet B and is 106 μm in the present example. In the laser length measuring system, the distance between a sensor and the surface of the stage 26 of the sheet conveying part 3 which tightly holds the back side of the sheet is set to zero in advance, and the distance from the sensor to the front side of the printed sheet is measured. The difference in distance is indirectly considered to be a thickness Z(t)[μm]. In the equation (3), Z* in the above-mentioned equation (1) is replaced by Zo.

From the conversion table of a thickness change rate and a moisture content inputted as the measurement information, each thickness change rate dZ(t) is converted into the moisture content dW(t)[g/m$^2$] (S111). More specifically, the thickness change rate dZ(t) with respect to the elapsed time t from printing obtained in S110 is converted into the moisture content dW by using the relationship as shown in Table 1. More specifically, the thickness change rate dZ(t) of 5.00, 4.00, 3.00, 2.00, or 1.00 as shown in Table 1 is converted into the moisture content dW of 5.11, 4.55, 3.82, 2.92, or 1.85, respectively. When the thickness change rate dZ(t) is a value other than those shown in Table 1, the moisture content dW is obtained by an interpolation operation.

Figure 10A:
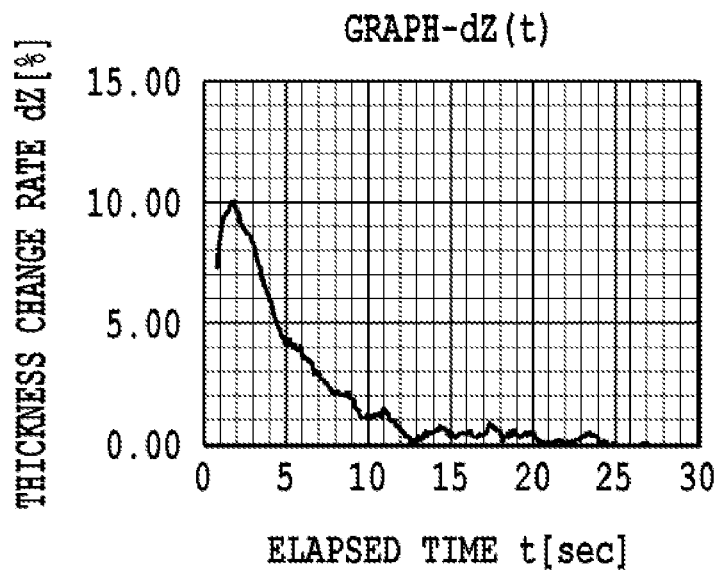
FIG. 10A and FIG. 10B illustrate exemplary displays showing a thickness change rate Z(t) and a change in moisture content dW(t) in a display unit.
Figure 10B:
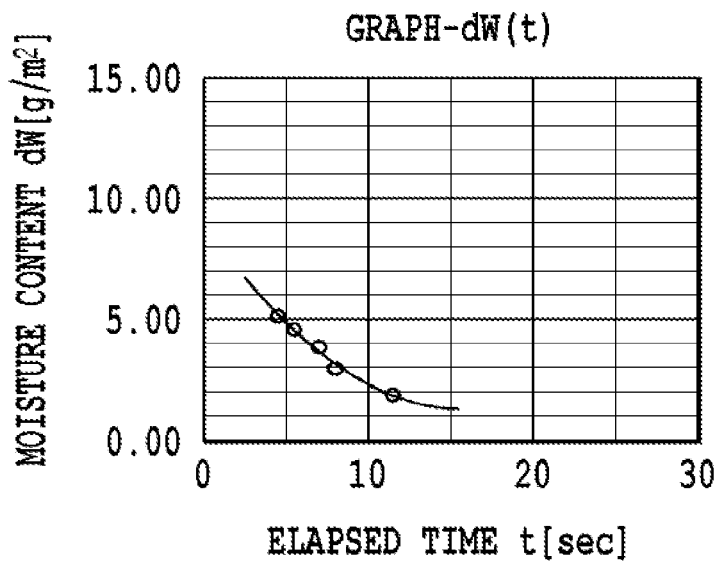

The change in thickness change rate dZ(t) and the change in decreasing moisture content dW(t) thus obtained along with an elapsed time are displayed on a display unit of the control part 4 as graphs, for example (S118). FIG. 10A and FIG. 10B illustrate exemplary displays showing the change in thickness change rate Z(t) and the change in moisture content dW(t), respectively, on a display unit. dZ(t) shown in FIG. 10A is a change in thickness change rate dZ based on a measurement value of the thickness after an elapsed time t from printing. dW(t) shown in FIG. 10B is a change in moisture content obtained based on the thickness change rate shown in FIG. 10A and Table 1. Here, with respect to the elapsed time t after which the thickness change rate dZ(t) of 5.00, 4.00, 3.00, 2.00, or 1.00 is obtained, the moisture content dW corresponding to the thickness change rate dZ(t) shown in Table 1 is plotted, and then an quadratic approximation curve is also shown.

(S113 to S116: Paper Discharging Step)

The print sheet D held by suction on the sheet conveying part 3 and conveyed to the paper discharging part is released from suction, and then stored in the sheet discharge part 6 by using a conveying mechanism such as a conveying roller.

According to the above-described first example, it is possible to estimate a moisture content by measuring a change in thickness of the print sheet after printing. Estimating a moisture content allows determination of a minimum drying time, a heating temperature, and a suction force required for printing a high-quality image on various types of print sheets such as coated print paper or coated paper.

Second Example

Figure 11:
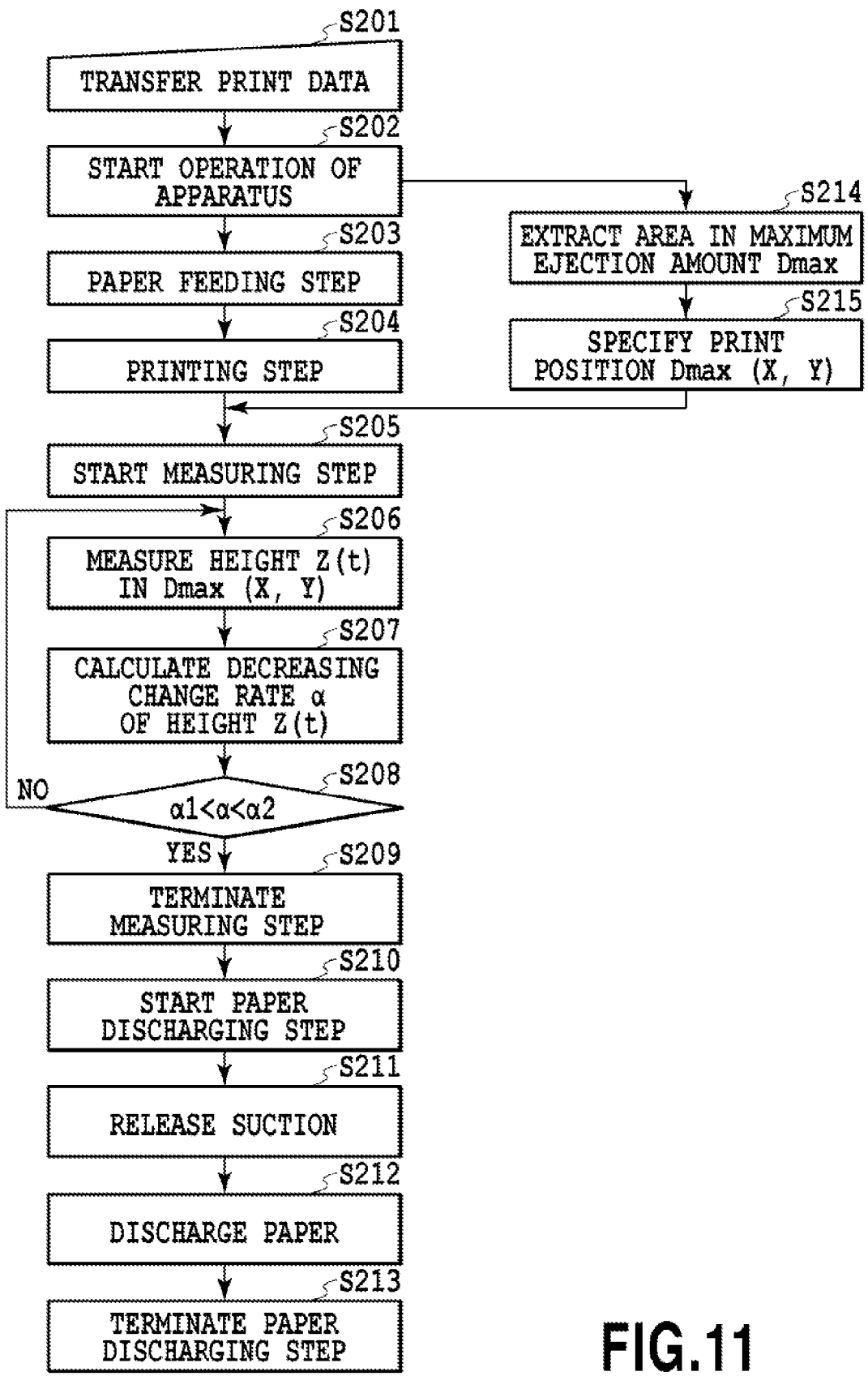
FIG. 11 is a flowchart of a process of reducing deformation of a print sheet based on a moisture content obtained by estimating the moisture content of the print sheet according to one embodiment of the present invention.

A second example of the present invention takes into consideration that the change in thickness of the print sheet and the moisture content, that is, the sheet deformation, are strongly correlated as described in the first example, and relates to the process of reducing deformation such as cockling by releasing the holding of the print sheet depending on the thickness change. FIG. 11 is a flowchart of this process. This process is also performed in the printing apparatus 10 that is made up by having the ink-jet printing part 1, the thickness measuring part 2, the sheet conveying part 3, and the control part 4 as shown in FIG. 1A and FIG. 1B. Hereinafter, the process of the present example will be described according to the steps in the order mentioned in FIG. 11. The description of the steps similar to the steps shown in FIG. 9 will be omitted.

(S201 to S202, S214 to S215: Print Data Transfer)

Print data is transferred by the controller in the control part 4 or an external device and is stored in memory. At the same time, the operation in the printing apparatus starts. An area in a maximum ejection amount Dmax is extracted from the transferred print data, and a print position Dmax (x, y) of the area Dmax is obtained (S214, S215).

(S205 to S209: Measuring Step)

The thickness measuring part 2 measures the height of the conveyed print sheet D held by suction on the stage 26 at a suction pressure of −10 kPa in the coordinate position Dmax (x, y) after an elapsed time t from printing, at predetermined intervals, and obtains Zt[µm] (S206). Furthermore, a decreasing change rate α [µm/s] per unit time of the height Zt[µm] obtained at predetermined intervals is obtained (S207). Then, it is determined whether the obtained decreasing change rate α and values α1 and α2 as specified in terms of cockling reduction (described later) satisfy the relationship of α1<α<α2 (S208). In a case where the decreasing change rate α obtained at predetermined intervals satisfies the above relationship, the measuring step is terminated (S209).

Note that the decreasing change rate α[µm/s] is preferably obtained as a change rate of a regression curve of Zt[µm] which decreases by time t unit, and can be obtained by the following general formula:

$$\alpha = (\Sigma(t - t_{ave})(Zt - Zt_{ave}))/\Sigma(t - t_{ave})^2 \quad (4)$$

(S210 to S213: Paper Discharging Step)

The print sheet D held by suction on the sheet conveying part 3 and conveyed to the sheet discharge part is released from holding by suction, and then stored in the sheet discharge part by using a conveying mechanism such as a conveying roller. In this case, the print sheet D is stored in a state in which cockling is reduced through the above-described steps.

Figure 12:
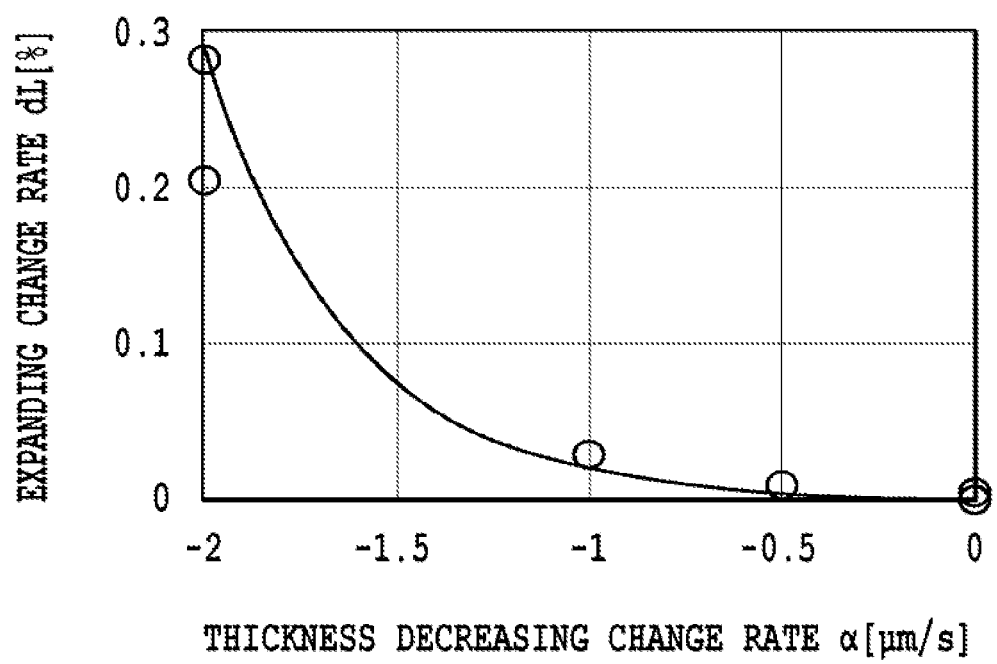
FIG. 12 is a graph used for explaining the way of defining $\alpha 1$ and $\alpha 2$ which represent a preferable range of a thickness decreasing change rate $\alpha$ used in the process of reducing sheet deformation shown in FIG. 11.

FIG. 12 is a graph used for explaining the way of defining α1 and α2 which represent a preferable range of the thickness decreasing change rate α.

In the same step as the printing step of FIG. 11, on a print sheet (e.g., New V Matt having a basis weight of 104.7 g/m² and a thickness of about 106 µm available from Mitsubishi Paper Mills Ltd.), a given test pattern image is printed by using the ink C containing 77% of pure water and 23% of others including a color material, for example. This printing is performed based on print data having the maximum ejection amount C3 (28 g/m²), for example. Then, with respect to the image thus printed, the effect of reducing cockling is evaluated in the following four cases: a case where α satisfying α1<α<α2 in connection with specified values α1, α2 is generally −2[µm/s], a case where α is generally −1[µm/s], a case where α is generally −0.5[µm/s], and a case where α is generally 0[µm/s]. In the evaluation of the effect of cockling reduction, the expanding change rate dL[%] is expressed by the following equation:

$$dL[\%] = (L2 - L1)/L1 \times 100 \quad (5)$$

Here, L1[mm] is a distance between two points in the print area of the maximum ejection amount C3 (28 g/m²), and L2[mm] is a length of the line along the surface on which the two points defining the distance L1 exist. In other words, L2 is longer than L1 as the cockling increases, and L2=L1 when the cockling is zero. Of course, the evaluation is performed in a state in which holding by suction of the sheet on the stage 26 is released.

As shown in FIG. 12, as the thickness decreasing change rate α[µm/s] decreases to reach substantially −2, the expanding change rate dL of the sheet released from the holding by suction decreases to dL=0.3~0.2[%]. Furthermore, as the decreasing change rate α[µm/s] decreases to reach substantially −1, the expanding change rate dL decreases to 0.1[%] or smaller. Furthermore, as the decreasing change rate α[µm/s] decreases −0.5 to 0, the expanding change rate dL becomes substantially zero.

As described above, in the present embodiment, it is possible to preferably reduce cockling when the thickness decreasing change rate α is within the above-described appropriate range between −2 and 0. In other words, after the decreasing change rate α reaches a value within the above-described range between −2 and 0, the printing operation requires releasing of the holding of the print sheet on the surface of the stage 26. Accordingly, when the expanding change rate dL before reaching the value within the range between −2 and 0 is large and cockling is very likely to occur, the surface of the print sheet is held on the stage 26 and the cockling is preferably reduced in a compulsory manner. As a result, occurrence of the cockling can be preferably reduced.

Third Example

Figure 13:
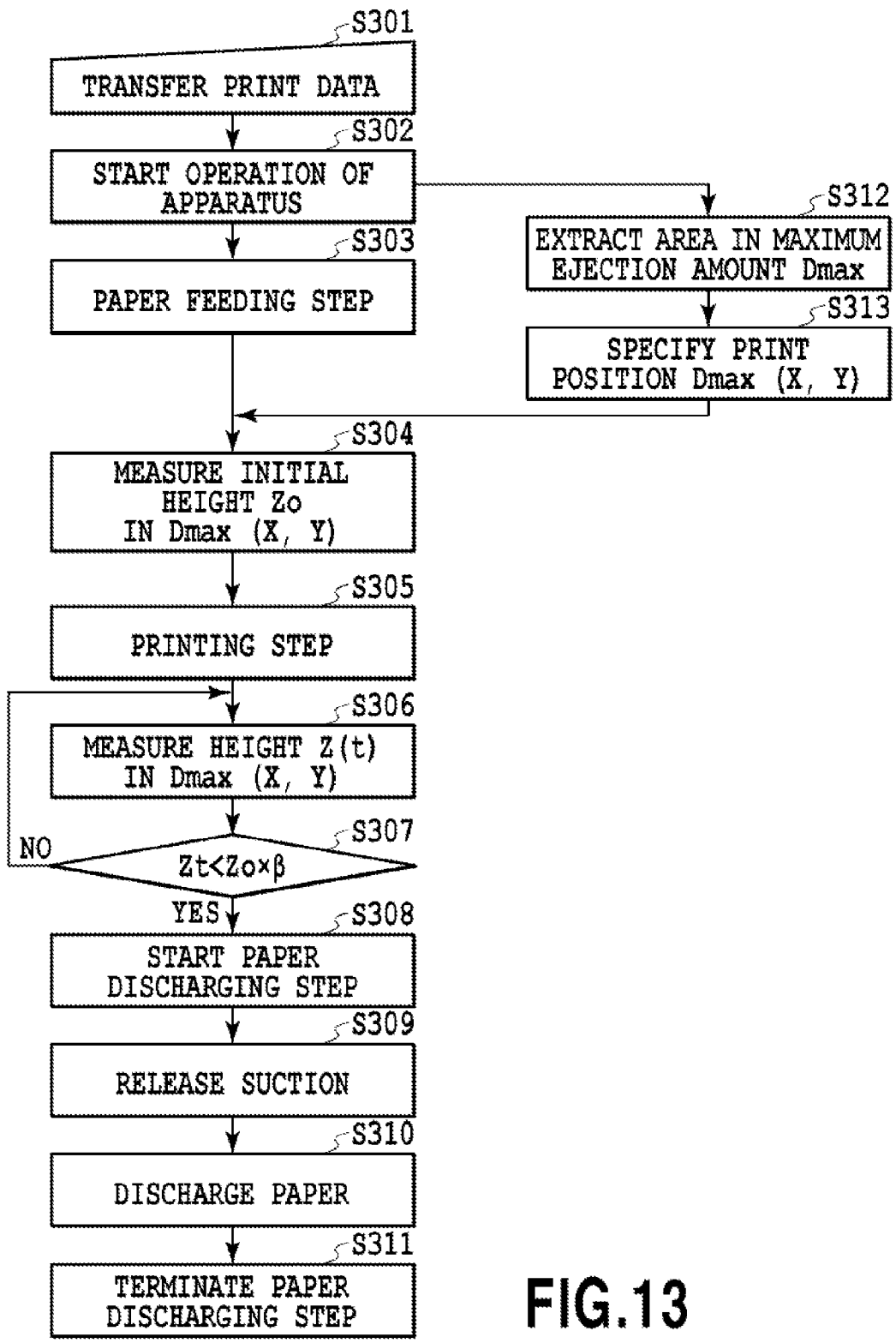
FIG. 13 is a flowchart of a process of releasing the holding of a print sheet in response to a thickness change according to a third example of the present invention.

A third example of the present invention takes into consideration that the change in thickness of the print sheet and the moisture content are strongly correlated and relates to the process of reducing cockling by releasing the holding of the print sheet depending on the thickness change, similarly to the second example. FIG. 13 is a flowchart of this process. This process is also performed in the printing apparatus 10 that is made up by Having the ink-jet printing part 1, the thickness measuring part 2, the sheet conveying part 3, and the control part 4 as shown in FIG. 1A and FIG. 1B. Hereinafter, the process of the present example will be described according to the steps in the order mentioned in FIG. 13. The description of the steps similar to the steps shown in FIG. 9 or FIG. 11 will be omitted.

(S301 to S302, S312 to S313: Print Data Transfer)

Print data is transferred by the controller in the control part 4 or an external device and stored in memory. At the same time, the operation in the printing apparatus is started. An area in a maximum ejection amount Dmax is extracted from the transferred print data, and a print position Dmax (x, y) of the area Dmax is obtained (S312, S313).

(S304: Measurement Before Printing)

Measurement is made on an initial height Zo in the print position Dmax (x, y). More specifically, the height before printing in the coordinate position Dmax (x, y) of the print sheet is measured, and Zo[μm] is thus obtained and stored in memory. In the laser length measuring system, the distance between a sensor and a surface of the stage 26 of the sheet conveying part 3 which tightly holds the back side of the sheet is set to zero in advance, and the distance from the sensor to the front side of the print sheet before printing is measured. The difference in distance is indirectly considered to be an initial height (thickness) Zo[μm].

(S306 to S307: Measuring Step)

The height in the position Dmax (x, y) of the print sheet D conveyed to the thickness measuring part 2 is measured at predetermined intervals, and the height (thickness) of the sheet Zt[μm] is obtained. This measurement is performed in the same manner as obtaining the initial height (thickness) Zo[μm]. As described before, a water component of ink applied to the sheet in the printing step penetrates into a base paper of the print sheet D to destroy paper fibers (cellulose), and the printed portion swells to be a swollen state by water absorption and then to a dry and shrunk state in which the paper fibers are restructured due to a decrease in the moisture content by drying. Accordingly, the height Zt relatively rapidly increases, then relatively rapidly decreases, and then gradually decreases. In a case where the decreased Zt satisfies the following relationship defined in terms of cockling reduction, the measurement is terminated:

$$Zt < Zo \times \beta$$

Here, β is a number not smaller than 1, and is specified within a range between 1.005 and 1.05 so that reduction of cockling can be visually recognized.

As described above, it is possible to reduce cockling of the print sheet by holding the print sheet until the thickness change rate (Zt/Zo) of the print sheet after printing decreases to a value equal to or smaller than a given value (β) like the above example. Accordingly, it is possible to print a high-quality image on various types of print sheets such as coated printing paper or coated paper in a minimum drying time required, and it is also possible to reduce cockling with less memory and easier computation by comparing the thickness of the print sheet before printing with the thickness of the print sheet after printing.

In the present example, the thickness measuring part is provided behind the printing part 1 in a conveying direction. However, a plurality of thickness measuring parts can be provided in front of and behind the printing part so that the sheet can be conveyed in a single direction, thereby improving productivity.

Fourth Example

A forth example of the present invention takes into consideration that the change in thickness of the print sheet and the moisture content are strongly correlated, and relates to the process of reducing deformation of the print sheet such as cockling by determining a maximum ejection amount depending on the thickness change.

Figure 14:
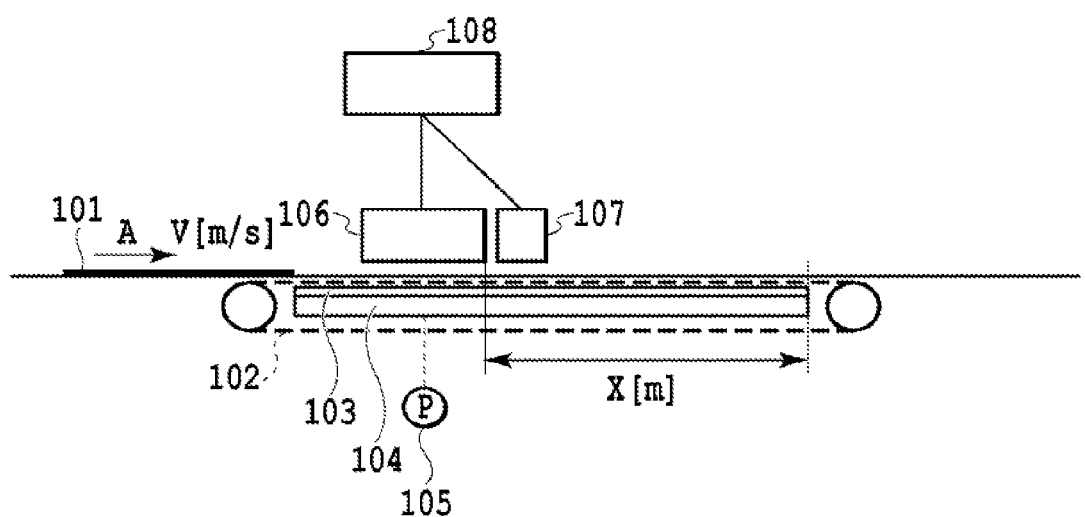
FIG. 14 is a cross-sectional view of a schematic structure of a printing apparatus according to a fourth example of the present invention.

FIG. 14 is a cross-sectional view of a schematic structure of the printing apparatus according to the fourth example of the present invention. FIG. 14 shows that in a conveying path, a print sheet 101 is sucked by a belt 102 in front of a printing part 106 and conveyed at V[m/s] in an arrow A direction. The suction is performed through a decompression chamber 104 decompressed by a vacuum pump 105, a belt support porous member 103, and a punching belt 102. While being in tight contact with the punching belt 102, the sucked print sheet 101 is conveyed, and ink is ejected in the printing part 106, and a test pattern for measuring a change amount of the thickness of the print sheet is printed. Then, the test pattern is conveyed immediately below a laser displacement gage 107 and stopped, and a change amount of the thickness of the print sheet is measured. Based on the measured change amount of thickness and an acceptable cockling value inputted by a user, a maximum ejection amount (described later) is determined and set. By using information on the maximum ejection amount thus obtained, actual printing is performed by the printing part 106.

The printing part 106 of the present example is a unit applying ink from a print head to a conveyed sheet to form an image. The print head is a line-type print head in which nozzles of the ink-jet type are arranged across an area corresponding to a maximum width of a sheet assumed to be used. A plurality of print heads is arranged in parallel in a sheet movement direction (conveying direction). For example, there are provided four print heads corresponding to four colors of ink: cyan, magenta, yellow, and black. Each color ink is supplied individually to the print head from an ink tank (not shown) via an ink tube.

For the suction system, a vacuum suction system is used in the present example. However, an electrostatic suction system can be used. In addition, for a thickness measuring system, the laser length measuring system is used in the present example. However, an optical interference system or the like can be used.

A control part 108 has a controller having a CPU, memory, and various I/O interfaces, and a user interface consisting of an input unit for a user to input and output various kinds of information and a display. Operation in the apparatus of the present invention is controlled by the controller in the control part or controlled based on instructions from an external device such as a host computer connected to the controller via I/O interfaces.

Figure 15:
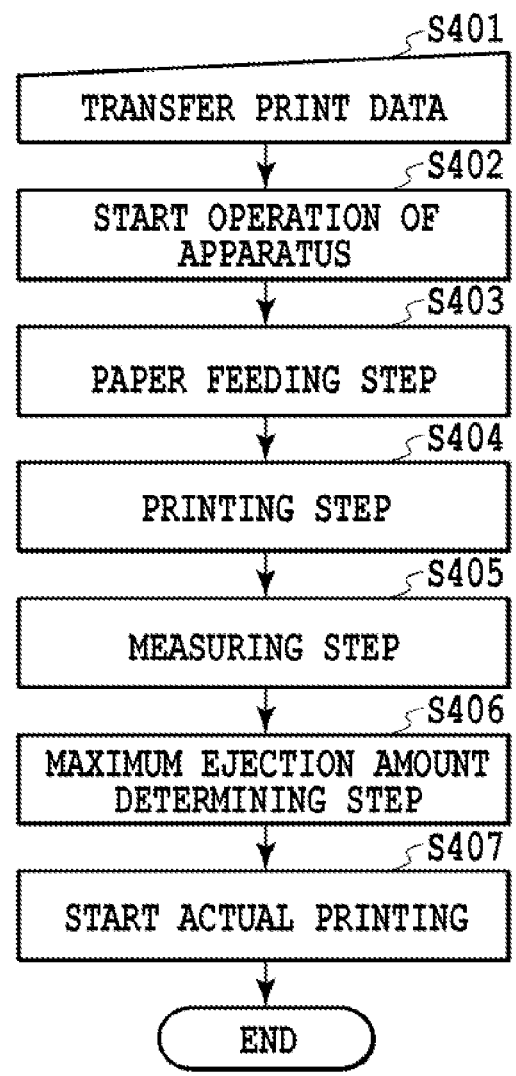
FIG. 15 is a flowchart of a process of determining a maximum ejection amount for reducing cockling according to the fourth example.

FIG. 15 is a flowchart of a process of determining a maximum ejection amount for reducing cockling according to the fourth example. This process will be described for each step.

(S401 to S402: Print Data Transfer)

Print data is transferred by the controller in the control part 108 or an external device such as a host computer connected to the controller via I/O interfaces and is stored in memory. Then, the operation and the processing in the printing apparatus are started by CPU operation.

(S403: Paper Feeding Step)

In the present example, the print sheet 101 is fed, conveyed, and held by suction on the punching belt which is heated to 70° C., for example, by the vacuum suction system at a pressure of −10 kPa.

(S404: Printing Step)

The printing part 106 applies ink from a print head based on the print data to print a test pattern image. The test pattern image consists of one or more portions having different ejection amounts. The image portion may be of any size as long as the change amount of thickness can be measured, for example, a size of 5 mm×5 mm. In the present example, a pattern of a 5 mm×5 mm square is printed in three ejection amounts, 6 g/m², 13 g/m², and 19 g/m².

(S405: Measuring Step)

The change in height of the print sheet 101 in a portion of the test pattern image printed in the printing step is measured at predetermined intervals, and Zt[μm] is obtained. Moisture of ink applied to the sheet in the printing step penetrates into a base paper of the print sheet 101 to destroy paper fibers (cellulose), and the printed portion swells to be a swollen state by water absorption and then to a dry and shrunk state in which the paper fibers are restructured due to a decrease in the moisture content in the drying step. In the present example, the printing step is performed three times in the above-mentioned three ejection amounts and every measurement is performed for 30 seconds by using the same measuring device. The same measurement results as those shown in FIG. 4 can be obtained.

(S406: Determine a Maximum Ejection Amount)

Figure 16:
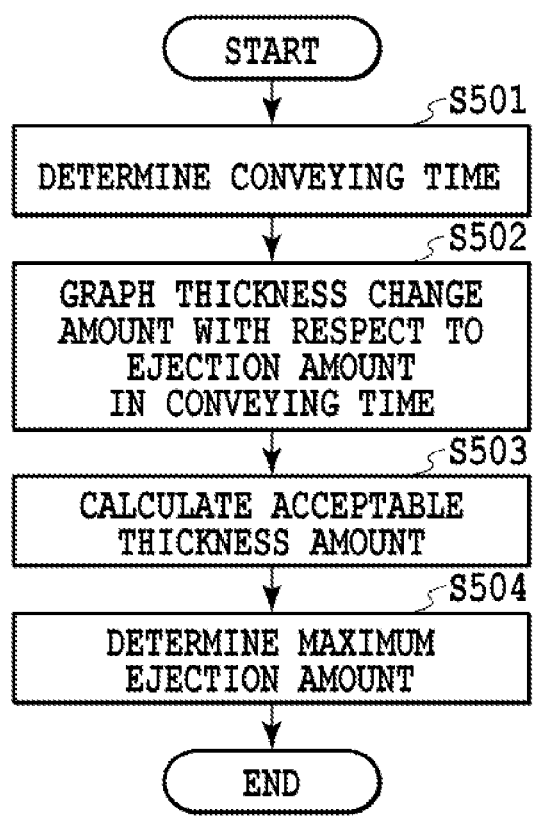
FIG. 16 is a flowchart describing in detail the step of determining the maximum ejection amount shown in FIG. 15.

FIG. 16 is a flowchart describing in detail the step of determining a maximum ejection amount. In FIG. 16, in S501, based on a conveying distance X from a point below the print head to a point at which the fixed conveyance of the print sheet is terminated when the belt releases the holding by suction and a conveying speed V of the print sheet, a conveying time T required to cover the distance X is calculated by the following equation:

$$T = X \div V \tag{6}$$

In the present example, the conveying distance X=4 m, the conveying speed V=0.5 m/s, and thus T=8 seconds.

Figure 17:
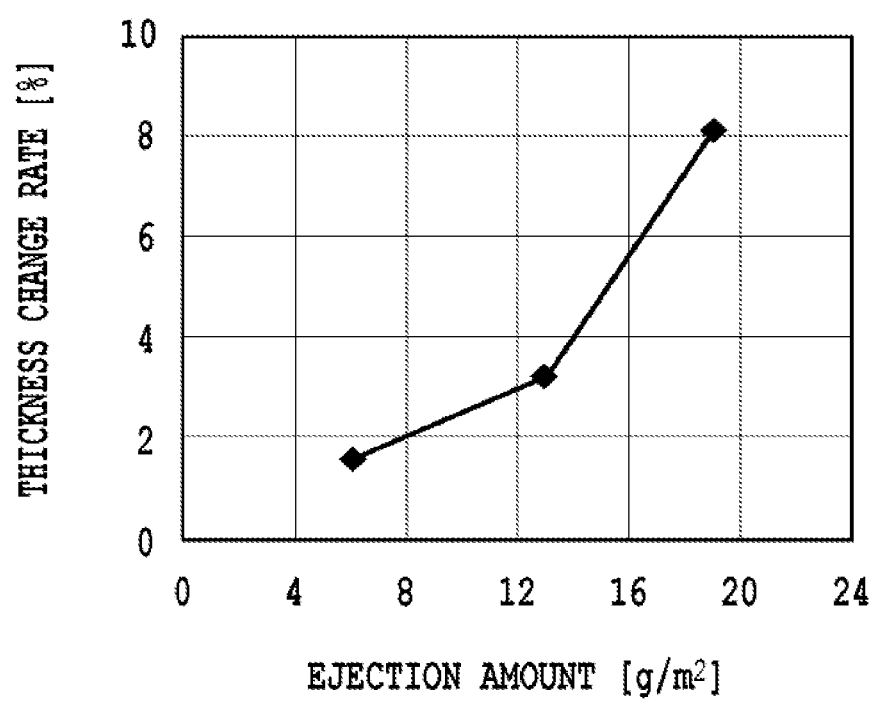
FIG. 17 is a graph showing the relationship between an ejection amount obtained in the step of determining the maximum ejection amount and a thickness change rate.
Figure 20:
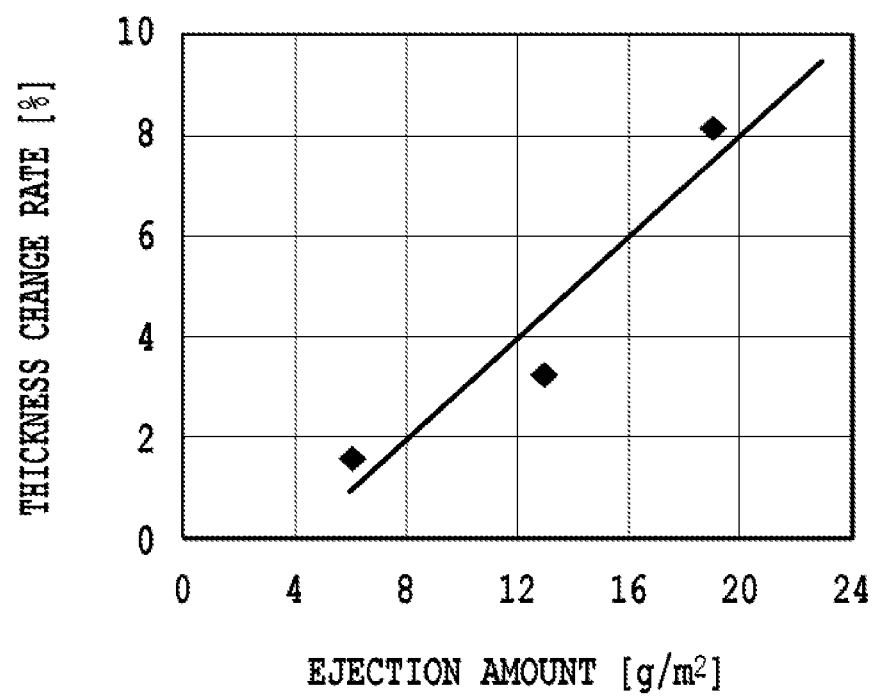
FIG. 20 shows an approximate straight line obtained from the relationship between the ejection amount and the thickness change rate shown in FIG. 17.

Then, in S502, based on the thickness change rate dZ in the conveying time T (8 seconds=elapsed time) with respect to the ejection amounts (A1, A2, and A3) as shown in FIG. 4A to FIG. 4C, the thickness change rate for each of the three ejection amounts is obtained. Based on them, the relationship between the ejection amount and the thickness change rate is obtained. FIG. 17 is a graph showing the relationship between the ejection amount and the thickness change rate. FIG. 20 shows the relationship in an approximate straight line obtained from the plotted relationship by a least square method. The thickness change rate can be obtained based on the equation (3) explained in Experiment 1 as described before.

Then, in S503, based on the acceptable cockling value C[ppm] inputted by the user, an acceptable thickness change rate dXa is calculated by the following equation:

$$dXa = C \div \beta \tag{7}$$

In the present example, the acceptable cockling value C=2000[ppm] and the coefficient β=400, and thus dXa=5 [%]. Here, although β varies depending on the type of print sheet, the value does not change greatly.

Figure 18:
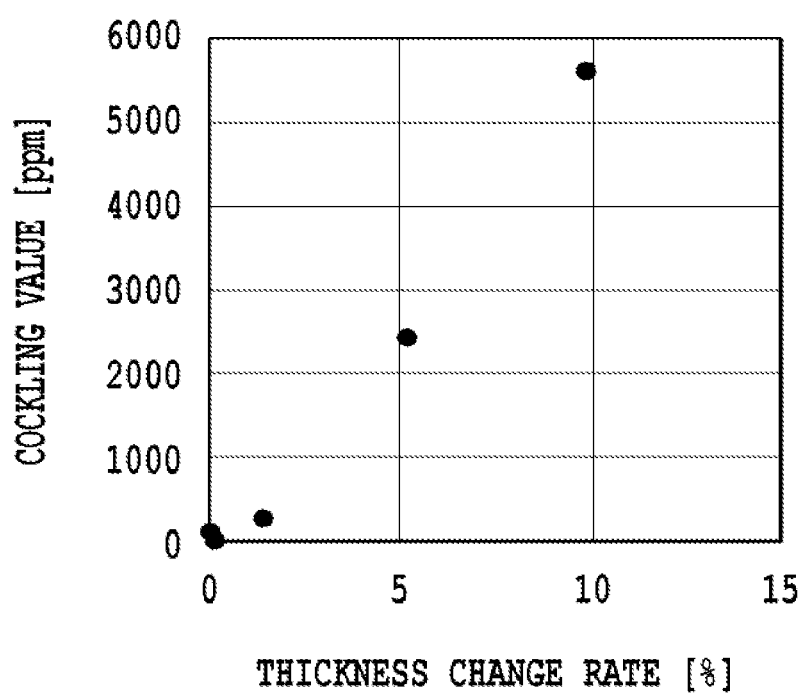
FIG. 18 is a graph showing the relationship between a cockling value and a thickness change rate according to the fourth example.

Note that the cockling value and the thickness change rate when a printed matter is created in the same ejection amount have a correlation as shown in FIG. 18. In this case, evaluation of cockling may also be performed by using the expanding change rate dL[%] as the cockling value in the equation (5) described in the second example. Accordingly, instead of using the equation for obtaining the thickness change rate dXa, it is possible to measure a cockling value and a thickness change rate beforehand and use the relationship obtained by plotting the cockling value with respect to the thickness change rate.

Figure 19:
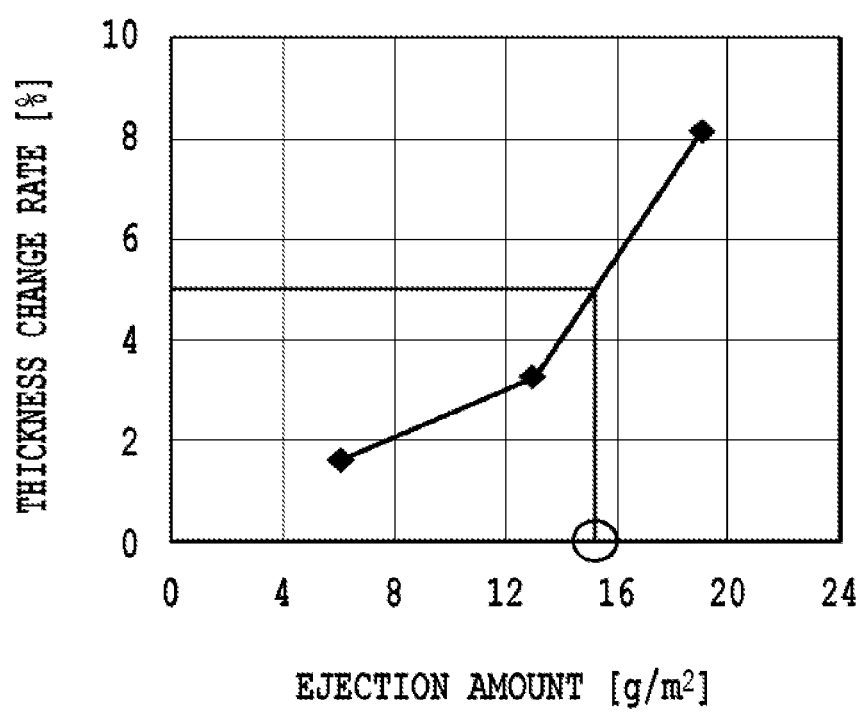
FIG. 19 is a graph illustrating a process of obtaining a maximum ejection amount from an acceptable thickness change rate dXa in the relationship between the thickness change rate and the ejection amount shown in FIG. 17.

Finally, in S504, in the relationship between the thickness change rate and the ejection amount (FIG. 17), the ejection amount corresponding to the acceptable thickness change rate dXa is obtained, as shown in FIG. 19, and the ejection amount is set as a maximum ejection amount. In the present example, since dXa is 5, the maximum ejection amount is about 15 g/m². Accordingly, the maximum ejection amount can be determined. Note that in determining the maximum ejection amount, instead of the relationship shown in FIG. 17, it is certainly possible to use the relationship shown in FIG. 20.

(S407: Actual Printing)

The maximum ejection amount thus determined is set to 16 g/m² in this example as a condition of printing operation, and the actual printing, that is, normal printing, is performed. Note that the limitation to the maximum ejection amount is performed for each ink color. This limitation is set in a manner that, for example, when generating ink color data of CMYK based on RGB image data, a signal value exceeding a signal value corresponding to the maximum ejection amount for each ink color is converted into a signal value corresponding to the maximum ejection amount. According to the actual printing of the present example limiting the maximum ejection amount, it is possible to obtain a preferable image in which cockling is appropriately reduced.

According to the above-described fourth example, measuring the change in thickness of the print sheet after printing allows determination of the maximum ejection amount of ink, thereby reducing deformation of sheets such as cockling after printing.

Fifth Example

In a fifth example of the present invention, unlike the fourth example, two laser displacement gages for measuring the sheet thickness before printing and the sheet thickness after printing are provided for a conveying path of the print sheet. This improves throughput.

Figure 21:
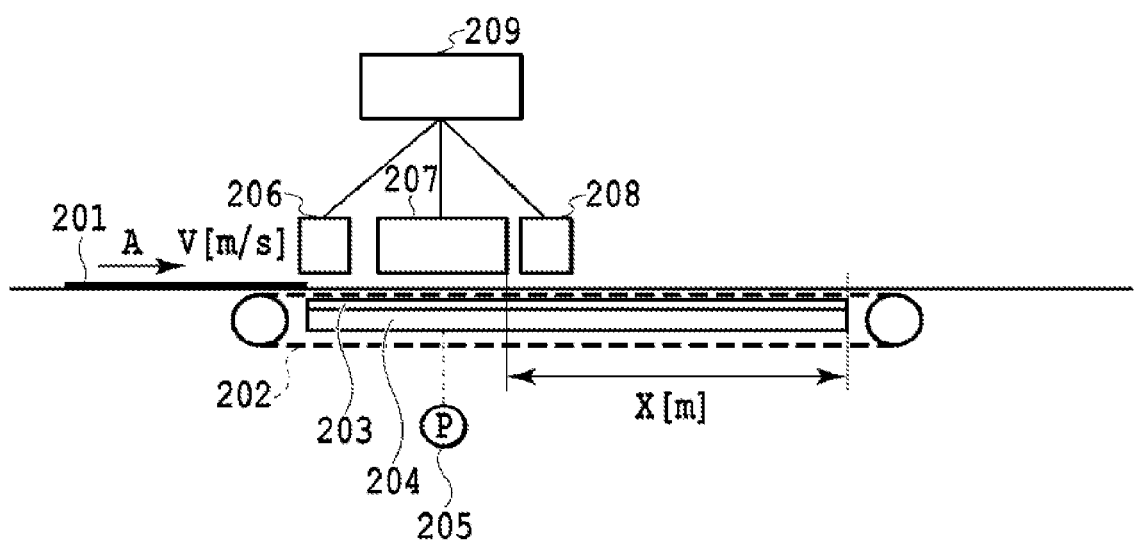
FIG. 21 is a cross-sectional view of a schematic structure of a printing apparatus according to a fifth example of the present invention.

FIG. 21 is a schematic cross-sectional view of a structure of the printing apparatus according to the fifth example of the present invention. In FIG. 21, the description of the elements similar to those shown in FIG. 14 according to the fourth example will be omitted. In the conveying path of a print sheet 201, a laser displacement gage 206 and a laser displacement gage 208 are provided upstream and downstream of a printing part 207, respectively. The print sheet 201 sucked and conveyed by a punching belt 202 is conveyed immediately below the upstream laser displacement gage 206, and the thickness of the print sheet before printing is measured. Then, a test pattern for measuring a change amount of the thickness of the print sheet is printed by the printing part 207. Then, the print sheet is conveyed immediately below the downstream laser displacement gage 208 and stopped, and a change amount of the thickness of the print sheet in the test pattern is measured.

Figure 22:
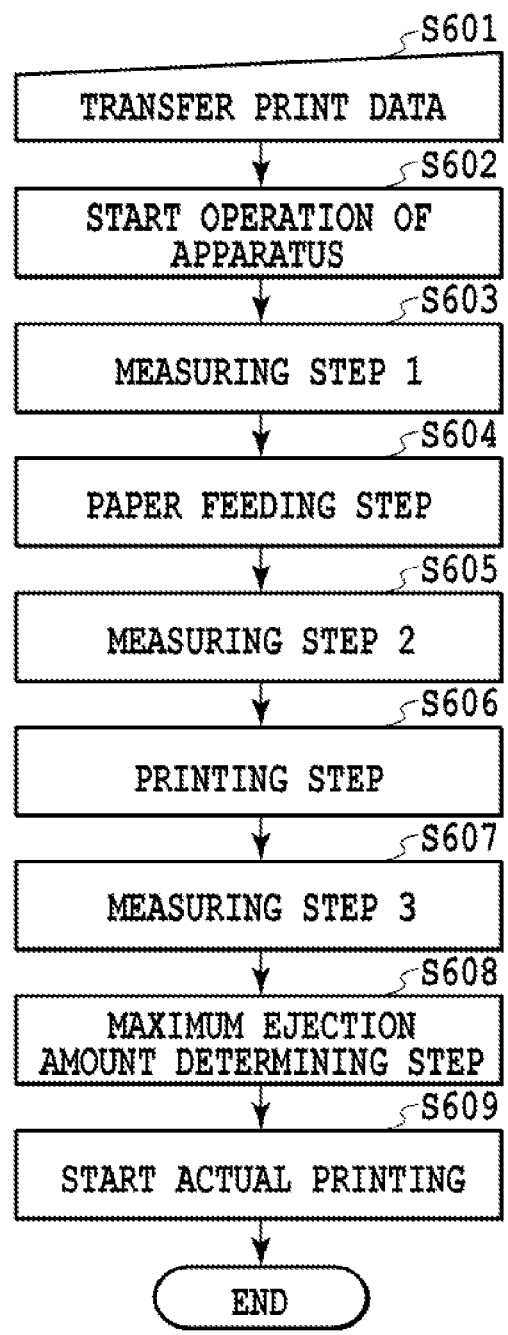
FIG. 22 is a flowchart of the entire process performed by the printing apparatus, including the step of determining a maximum ejection amount according to the fifth example.

FIG. 22 is a flowchart of the entire process performed by the printing apparatus, including the step of determining a maximum ejection amount according to the present example. In FIG. 22, the description of the steps corresponding to those shown in FIG. 15 according to the fourth example will be omitted.

(S603: Measuring Step 1)

The distance to the punching belt is measured by using the laser displacement gage 206 and the laser displacement gage 208. The measurement value obtained by the laser displacement gage 206 is set as $Za0$ and the measurement value obtained by the laser displacement gage 208 is set as $Zb0$.

(S605: Measuring Step 2)

The distance to the front side of the print sheet sucked by the belt is measured by the laser displacement gage 206, and the measurement value is set as $Za1$.

(S607: Measuring Step 3)

While being held by suction by the printing part 207, the print sheet on which the test pattern for measuring a thickness is printed is conveyed to the downstream laser displacement gage 208, and the change in height of the print sheet 201 in a printed test pattern portion is measured at predetermined intervals. The measurement value is set as $Zbt$.

(S608: Determine a Maximum Ejection Amount)

Based on values measured in the measuring steps 1, 2, and 3, $Zo$ and $Zt(Z(t))$ which are the parameters for determining a maximum ejection amount are obtained by the following equations:

$$Zo = Za0 - Za1 \quad (8)$$

$$Zt = Zb0 - Zbt \quad (9)$$

Then, the thickness change rate $dZ(t)$ is obtained by the equation (3) described in Experiment 1 to determine the maximum ejection amount according to the process described with reference to FIG. 16 according to the fourth example.

As a modification example of the fourth and fifth examples, the maximum ejection amount may be determined based on the acceptable thickness change rate. The fourth and fifth examples relate to examples in which a user inputs an acceptable cockling value. Inputting by the user an acceptable value of the thickness change rate with respect to the print sheet allows calculation of the maximum ejection amount without the processing in S503 of FIG. 16.

Sixth Example

A sixth example of the present invention takes into consideration that the change in thickness of the print sheet and the moisture content are strongly correlated, and relates to the process of reducing deformation of the print sheet such as cockling by determining a drying condition depending on the thickness change.

Figure 23:
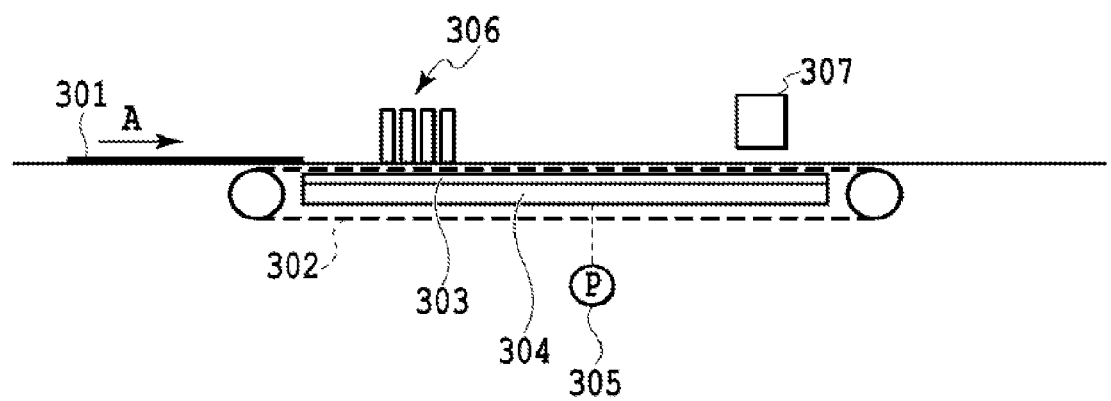
FIG. 23 is a cross-sectional view of a schematic structure of a printing apparatus according to a sixth example of the present invention.

FIG. 23 is a cross-sectional view of a schematic structure of a printing apparatus according to the sixth example of the present invention. In FIG. 23, a print sheet 301 is sucked and held in front of a printing part 306 and conveyed in an arrow A direction. The suction is performed through a decompression chamber 304 decompressed by a vacuum pump 305, a belt support porous member 303, and a punching belt 302. The belt support porous member 303 is heated as needed by a sheet-like heater (not shown), and while being in tight contact with the punching belt 302, the sucked print sheet 301 is heated to a desirable temperature and conveyed. In other words, the belt 302 of the present example also serves as a drying mechanism. On the print sheet thus conveyed, the printing part 306 prints two types of test patterns for measuring a change amount of thickness or a normal print image. The printing part 306 of the present example has four print heads corresponding to four colors of ink: cyan, magenta, yellow, and black, like the above-described examples.

The sheet having the test patterns printed thereon is conveyed immediately below a laser displacement gage 307 and stopped, and a change amount of the thickness of the print sheet is measured. As will be described later, the measured change amount of thickness is used to obtain a decreasing change rate $\alpha$ of the thickness of the print sheet. Based on the decreasing change rate and the state of the cockling by a visual check, a threshold $\beta$ of the decreasing change rate at which the effect of cockling reduction can be visually recognized is determined. In addition, an optimum drying condition is determined based on the thickness change rate obtained from another pattern.

Figure 24:
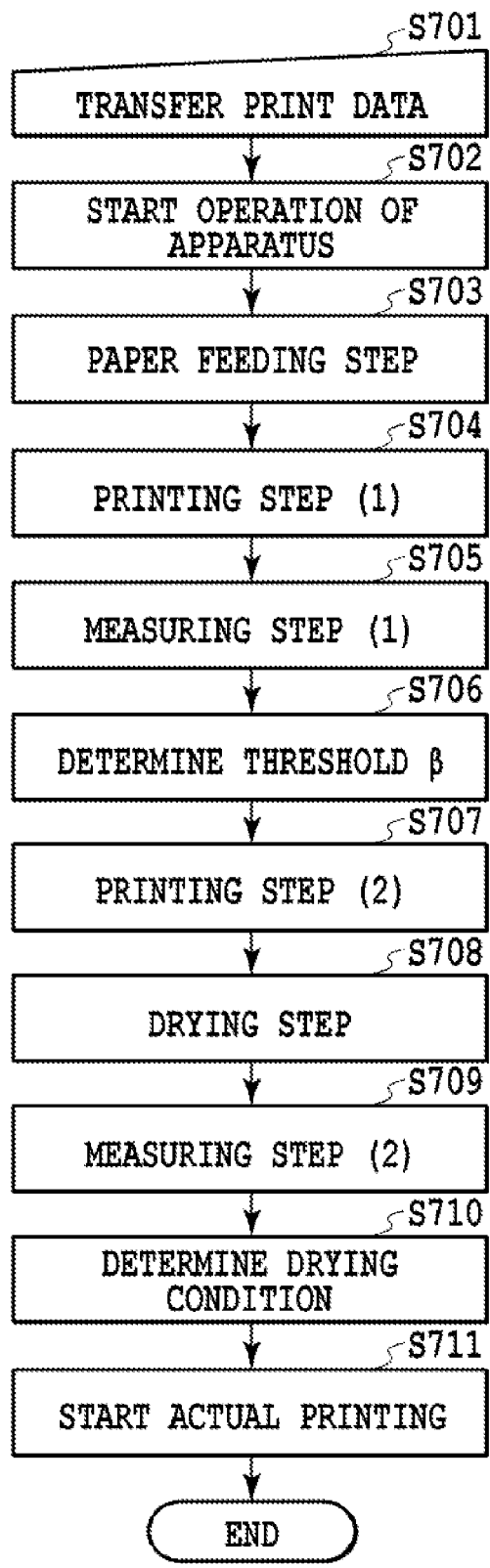
FIG. 24 is a flowchart of a process including the step of determining a drying condition in the printing apparatus of the sixth example.

FIG. 24 is a flowchart of a process including the step of determining a drying condition in the printing apparatus of the present example. The description of the steps corresponding to the steps shown in the above-described examples will be omitted.

(S704: Printing Step 1)

Based on the print data, ink is ejected from the print head of the printing part 306 to print test patterns. To change the decreasing change rate of the sheet thickness at various levels, for example, the volume of ink applied to the sheet is varied at a plurality of levels. The test patterns may be of any size as long as the cockling can be visually recognized, for example, a size of 10 mm×50 mm.

(S705: Measuring Step 1)

The height (thickness) of the print sheet 301 in a plurality of test pattern portions printed in the printing step 1 is measured at predetermined intervals, and is set as $Zt[\mu m]$. Moisture of ink applied in the printing step 1 penetrates into a base paper of the print sheet 301 to destroy paper fibers (cellulose), and the printed portion swells to be a swollen state by water absorption and then to a shrunk state in which the paper fibers are restructured due to a decrease in the moisture content along with a lapse of time. Accordingly, in a case where an ink application volume is small and a moisture content is small, the change amount of Zt is small and decreases gradually. On the other hand, in a case where an ink application volume is large and a moisture content is large, Zt relatively rapidly increases, then relatively rapidly decreases, and then gradually decreases. For example, Zt is measured for 10 seconds at predetermined intervals, and then the measurement is terminated. The decreasing change rate per unit time of Zt at this point is set as $\alpha[\mu m/s]$.

(S706: Determine a Threshold $\beta$)

After 10 seconds from the end of the printing step 1, suction of the print sheet by the belt is released and the current decreasing change rate $\alpha$ of each test pattern at this point is stored in memory. Meanwhile, the test patterns at the time of releasing suction are recognized by a visual check to determine whether cockling exists. Since the decreasing change rate α is a negative value, in a case where the decreasing change rate α is large, a decreasing amount of thickness is small. Accordingly, the cockling can be visually recognized when the decreasing change rate α falls below a certain value. As the decreasing change rate α falls far below the certain value, the cockling becomes worse as the decreasing change rate α decreases to lose texture. The smallest decreasing change rate α within the range of the decreasing change rate α at which cockling is at an acceptable level by a visual check is set as a threshold β.

(S707: Printing Step 2)

Ink is ejected from a print head to print a test pattern that is different from the ones printed in the printing step 1. In this step, the maximum ejection amount in the print data used in the actual printing in the subsequent step (S711) is set as a maximum ejection amount of ink when printing a test pattern in the present step. The test pattern may be of any size as long as the change amount of thickness can be measured, for example, a size of 5 mm×5 mm.

(S708: Drying Step)

In the printing step 2, the print sheet is dried by the belt 302 of the present example which also serves as a drying mechanism. In this drying step, it is possible to change the level of drying, whereby an optimum drying condition is set to reduce energy consumption. In the present example in which the print sheet is heated from the back side by a heater that is in tight contact with the print sheet, drying levels are changed according to the power supplied to the heater. When the print sheet is dried from the printed side, it is possible to use a hot air application, an infrared lamp, or the like. In this case, drying levels can be changed depending on hot air temperature, air velocity, amount of power, or the like. Alternatively, it is also possible to heat the print sheet from the back side and from the printed side at the same time.

(S709: Measuring Step 2)

The change in height (thickness) of the print sheet 301 in the test pattern portion provided in the printing step 2 is measured at predetermined intervals, and Zt[μm] is obtained. In a case where the print sheet 301 to which ink is applied and printing is performed in the printing step 2 is sufficiently dried, the thickness Zt does not substantially change or otherwise decreases gradually. This is because moisture of the applied ink causes paper fibers (cellulose) to be destroyed, and the printed portion swells to be a swollen state by water absorption and then to a dry and shrunk state in which the paper fibers are restructured due to a decrease in the moisture content in the drying step. Meanwhile, in a case where the print sheet is not sufficiently dried or does not dry, the thickness Zt relatively rapidly increases, then rapidly decreases, and then gradually decreases. Also in this step, the thickness Zt is measured for 10 seconds at predetermined intervals. The decreasing change rate per unit time of Zt at this point is set as α[μm/s].

(S710: Determine a Drying Condition)

In the printing step 2, as described above, drying is performed along with the printing of the test pattern. In the drying step, drying conditions of different drying levels are set as, for example, a1, a2, a3, . . . , an, in the order of the drying level from lowest to highest (a1<a2< . . . an), and in the printing step 2, the test pattern is printed for each drying condition. Then, the decreasing change rate α after, for example, 10 seconds from the end of the printing of the test pattern for each drying condition is obtained in the measuring step 2. The decreasing change rate for each drying condition is set as α10(a1), α10(2a), . . . , α10(an). As will be described later, in a case where the relationship between α10(an) and the threshold β satisfies, for example, α10(a3)<β<α10(a4), a4 is selected and set as the drying condition for the actual printing.

Next, a description will be given of a process of determining a drying condition based on the above-described process of determining a threshold β of the thickness decreasing change rate at which cockling does not occur and the threshold β. The following description is based on the result of printing the print sheet D with the ink C in the process described with reference to FIG. 9. The print sheet D is, for example, New V Matt having a basis weight of 104.7 g/m² (thickness of about 106 μm) available from Mitsubishi Paper Mills Ltd., and the ink C is a general ink containing a color material component, and, for example, contains 77% of pure water and 23% of others including a color material.

For each of the ink ejection amounts of 4 g/m², 7 g/m², 14 g/m², 21 g/m², and 28 g/m², print data for a test pattern of 10 mm×50 mm is used. Then, the print sheet D is held by suction on the sheet conveying part 3 (FIG. 1A and FIG. 1B) at a suction pressure of −10 kPa, followed by the printing step, and the decreasing change rate α is obtained in the measuring step.

FIG. 25 shows a thickness decreasing change rate α when the suction is released after 10 seconds from the end of the printing and a determination result of cockling by a visual check of the print sheet after the release of the suction for each of the ejection amounts. The visual determination is carried out by three people. Determination results are shown by "○", "x", and "Δ", respectively, for the case where none of three people can visually recognize the cockling, the case where all of three people can visually recognize the cockling, and the case where at least one of three people can visually recognize the cockling. As shown in FIG. 25, the decreasing change rate α decreases from −0.5 to −3.5. When α is not greater than −1, the visual determination is "○". When α reaches −1.2, the visual determination is "Δ" because some can recognize the cockling, but others cannot. When α falls below −1.2, the cockling can be visually recognized and the visual determination is "x". Based on the results, the threshold of the decreasing change rate can be determined to be β=−1.

Then, based on the image data for the actual printing, it is determined that the maximum ink ejection amount of the full-scale print image is 28 g/m², and print data for the test pattern in the ink ejection amount of 28 g/m² is created. Then, based on the print data for the test pattern, the print sheet D is dried to room temperature (drying condition of a1) and held by suction on the sheet conveying part at a suction pressure of −10 kPa, and the pattern is printed. Then, in the measuring step, based on the measurement result of the pattern, the decreasing change rate α after 10 seconds from the end of printing is obtained. Similarly, the print sheet D is dried to 50° C. (drying condition of a2), 70° C. (drying condition of a3), 90° C. (drying condition of a4), and 110° C. (drying condition of a5) so that the drying levels are changed. Using the same conditions other than the drying condition of room temperature, the printing step and the measuring step are performed.

FIG. 26 shows the relationship between a temperature of the print sheet (drying condition) and the obtained decreasing change rate α at this stage. As shown in FIG. 26, as the drying condition of the print sheet D changes from a1 (room temperature) to a5 (110° C.) to increase the drying level, the decreasing change rate α increases. Since the change in thickness of the print sheet is correlated with cockling, the greater the thickness decreasing change rate α (the smaller the absolute value of α), the greater the effect of cockling reduction. Accordingly, it is assumed that whether or not cockling occurs in, for example, the printed matter of the actual printing in which the maximum ink ejection amount is 28 g/m² depends on the threshold determined in the above-described manner, that is, β=−1. More specifically, in the present example, the drying condition for the threshold β=−1 is a3 in which the drying temperature of the print sheet is 70° C. Thus, a3 is determined to be the drying condition. As a result, the actual printing is performed such that the time from the end of printing to the release of suction is 10 seconds. Accordingly, it is possible to obtain a print image in which cockling is appropriately reduced.

With the drying condition thus obtained, the actual printing is performed until the image to be printed or the print sheet is changed. When another actual printing is performed subsequently, it is preferable to determine the threshold β in the same manner to determine the drying condition. However, in a case where the same print sheet is used, for example, the threshold β can be constant, whereas in a case where different images are printed on the same print sheet, it is possible to omit the step of determining the threshold β. In a case where a frequently-used print sheet is used, it is also possible to determine in advance at a plant or the like the threshold β or a drying condition determined based on the threshold β, and store them in memory in advance and use them.

Comparative Example

The actual printing (normal printing) of the sixth example is performed with the drying conditions a2 and a4 in which the drying temperatures of the print sheet were 50° C. and 90° C., respectively. The printed matter is visually checked and the presence or absence of the cockling is determined.

According to the sixth example, the thickness decreasing change rate α for a drying temperature of 50° C. is −2 and the thickness decreasing change rate α for a drying temperature of 90° C. is −0.5. In a case where the drying condition was 50° C., cockling was visually recognized in a portion printed with a maximum ejection amount of 28 g/m² and the texture of the printed matter is lost. In a case where the drying condition was 90° C., cockling was not visually recognized and a preferable printed matter was obtained. However, the power consumption required for drying is increased by about 40% as compared to the case where the drying condition was 70° C.

As described in the sixth example and the comparative example, the change in thickness of the print sheet after printing is measured and an appropriate drying condition is set so that cockling is reduced while the energy consumption is reduced, thereby allowing high-speed printing of a high-quality image on various types of print sheets such as print coated paper or coated paper.

Seventh Example

Figure 27:
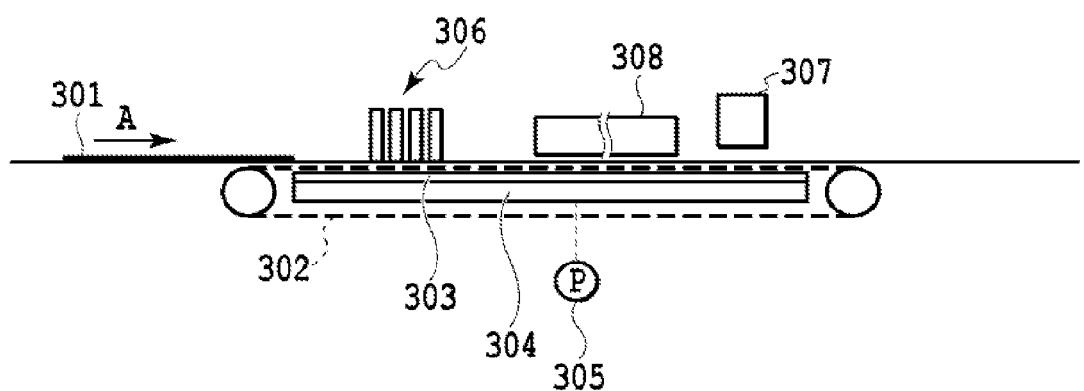
FIG. 27 is a side cross-sectional view of a structure of a printing apparatus according to a seventh example of the present invention.

FIG. 27 is a side cross-sectional view of a structure of a printing apparatus according to a seventh example of the present invention. In FIG. 27, the description of the elements similar to those according to the sixth example shown in FIG. 23 will be omitted. The difference between the sixth example and the seventh example in terms of elements is that a dryer 308 is provided downstream of the printing part 306 as a drying mechanism. This dryer 308 is used concurrently with the belt which heats the print sheet by suction.

Since the present example uses the same print sheet and the same image data for the actual printing as those in the sixth example, the threshold β is −1, and the maximum ink ejection amount is 28 g/m². In the same manner as the sixth example, print data for a test pattern of this maximum ejection amount is created. Then, based on the print data, the print sheet D is heated to 70° C. and held by suction on the print sheet conveying part at a suction pressure of −10 kPa, and a test pattern is printed. The thickness of the test pattern is measured and then the decreasing change rate α is obtained.

In the drying step, heating of the print sheet through the belt and airflow (hot air) from the dryer 308 are used at the same time for drying. The airflow of an air velocity of 5 m/s is blown to the print sheet D by the dryer 308, and a temperature immediately above the print sheet is set to room temperature (drying condition of b1), 50° C. (drying condition of b2), 70° C. (drying condition of b3), and 90° C. (drying condition of b4) so that the drying levels are change.

FIG. 28 shows the relationship between a temperature of airflow immediately above the print sheet (drying condition) at this stage and the decreasing change rate α after four seconds from the end of printing. As shown in FIG. 28, as the drying condition changes from b1 to b4 to increase the drying level, the decreasing change rate α increases. The greater the thickness decreasing change rate α, the greater the effect of cockling reduction. Accordingly, it is assumed that whether or not cockling occurs in, for example, the printed matter of the actual printing in which the maximum ink ejection amount is 28 g/m² depends on the threshold β=−1. More specifically, in the present example, the drying condition for the threshold β=−1 is b3 in which the drying temperature immediately above the print sheet is 70° C. Thus, b3 is determined to be the hot-air drying condition. The actual printing is performed such that the time from the end of printing to the release of suction is four seconds. As a result, it is possible to obtain a preferable image in which cockling is appropriately reduced.

In this manner, according to the present example, adding the hot-air drying to the heating of the print sheet makes it possible to reduce the time to the release of suction, thereby improving throughput of the actual printing.

Eighth Example

An eighth example of the present invention takes into consideration that the change in thickness of the print sheet and the moisture content are strongly correlated, and relates to the process of reducing deformation of the print sheet such as cockling by determining a suction force of the print sheet depending on the thickness change. More specifically, as described above in the sixth example, the belt itself for conveying the print sheet by suction is heated, and the print sheet is dried by the belt. Since the level of drying with the belt depends on the suction force, sheet deformation such as cockling can be reduced by appropriately determining a suction condition.

The structure of a printing apparatus according to the present example is the same as the one shown in FIG. 23 according to the sixth example. More specifically, the sheet having a test pattern printed thereon is conveyed immediately below the laser displacement gage 307 and stopped, and a change amount of the thickness of the print sheet is measured. The measured change amount of thickness is used to obtain a decreasing change rate α of the thickness of the print sheet. Based on the decreasing change rate and the state of the cockling by a visual check, a threshold β of the decreasing change rate at which the effect of cockling reduction can be visually recognized is determined. In addition, an optimum suction condition is determined based on the thickness change rate obtained from another pattern.

Figure 29:
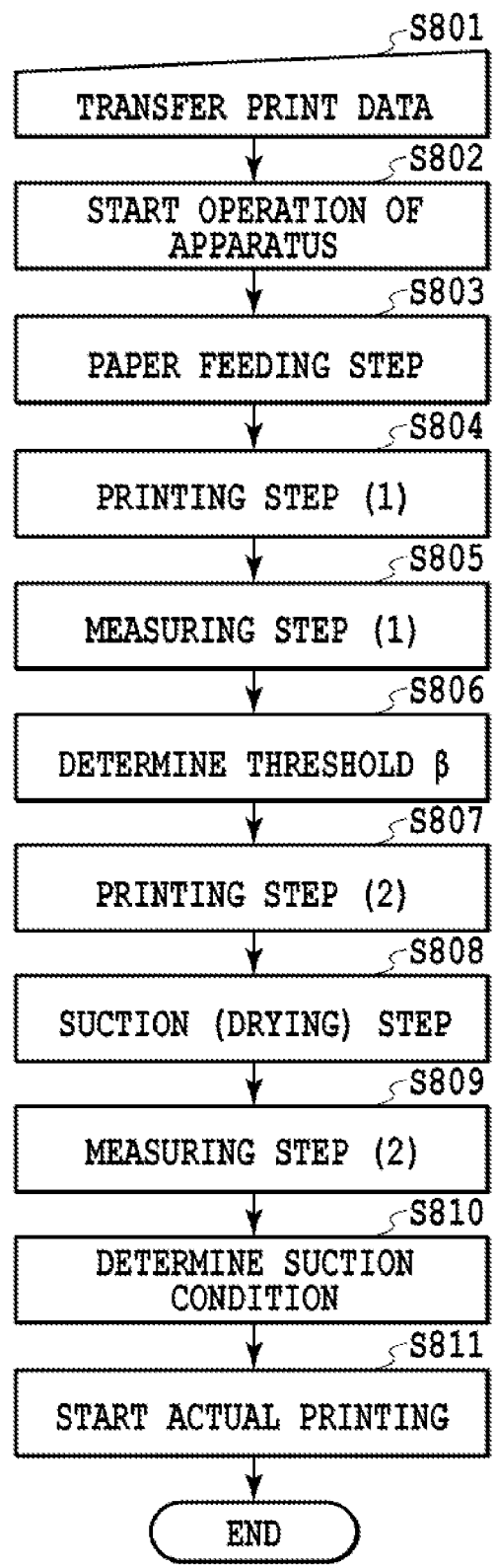
FIG. 29 is a flowchart of a process including the step of determining a suction condition in a printing apparatus according to an eighth example of the preset invention.

FIG. 29 is a flowchart of a process including the step of determining a suction condition in the printing apparatus according to the present example. The description of the steps corresponding to those according to the above-described examples will be omitted. A threshold β is determined through the same process as those (S701 to S706) of FIG. 24 according to the sixth example (S801 to S806). The "printing step 2" is performed through the same process as the step (S707) of FIG. 24 (S807).

In S808, the suction (drying) step according to the present example is performed. More specifically, in the printing step 2, while the belt 302 of the present example serving as the drying mechanism holds the print sheet by suction, the print sheet is dried. In the drying step, it is possible to change the suction force by the belt 302 to change the drying level, whereby an optimum drying condition is set to reduce energy consumption. Then, in the following "measuring step 2", the same process as the process (S709) of FIG. 24 is performed (S809).

In S810, the step of "determining a suction condition" is performed. More specifically, in the suction step (drying step), conditions of different suction levels by the belt 302 are set as a1, a2, a3, . . . , an, in the order of the suction level from lowest to highest (a1<a2< . . . an), and in the printing step 2, the test pattern is printed for each suction condition. Then, the decreasing change rate α after, for example, 10 seconds from the end of the printing of the test pattern for each suction condition is obtained in the measuring step 2. The decreasing change rate for each drying condition is set as α10(a1), α10(2a), . . . , α10(an). As will be described later, in a case where the relationship between α10(an) and the threshold β satisfies, for example, α10(a3)<β<α10(a4), a4 is selected and set as the suction condition for the actual printing.

Next, a description will be given of a process of determining a suction condition based on the above-described process of determining a threshold β of the thickness decreasing change rate at which cockling does not occur and the threshold β. The following description is based on the result of printing the print sheet D with the ink C in the process described with reference to FIG. 9. The print sheet D is, for example, New V Matt having a basis weight of 104.7 g/m² (thickness of about 106 μm) available from Mitsubishi Paper Mills Ltd., and the ink C is a general ink containing a color material component, and, for example, contains 77% of pure water and 23% of others including a color material.

For each of the ink ejection amounts of 4 g/m², 7 g/m², 14 g/m², 21 g/m², and 28 g/m², print data for a test pattern of 10 mm×50 mm is used. Then, the print sheet D is held by suction on the sheet conveying part 3 (FIG. 1A and FIG. 1B) at a suction pressure of −10 kPa, followed by the printing step, and the decreasing change rate α is obtained in the measuring step.

FIG. 25 as described in the seventh example, for example, shows a thickness decreasing change rate α when the suction is released after 10 seconds from the end of the printing and a determination result of cockling by a visual check of the print sheet after the release of the suction. The visual determination is carried out by three people. Determination results are shown by "○", "×", and "Δ", respectively, for the case where none of three people can visually recognize the cockling, the case where all of three people can visually recognize the cockling, and the case where at least one of three people can visually recognize the cockling. As shown in FIG. 25, the decreasing change rate α decreases from −0.5 to −3.5. When α is not greater than −1, the visual determination is "○". When α reaches −1.2, the visual determination is "Δ" because some can recognize the cockling, but others cannot. When α falls below −1.2, the cockling can be visually recognized and the visual determination is "×". Based on the results, the threshold of the decreasing change rate can be determined to be β=−1.

Next, based on the image data for the actual printing, it is determined that the maximum ink ejection amount of the full-scale print image is 28 g/m², and print data for the test pattern in the ink ejection amount of 28 g/m² is created. Then, based on the print data for the test pattern, the print sheet D is dried to room temperature and held without suction (suction condition of a1) on the sheet conveying part, and the pattern is print. Then, in the measuring step, based on the measurement result of the pattern, the decreasing change rate α after 10 seconds from the end of printing is obtained. Similarly, the print sheet D is sucked at a suction pressure of −10 kPa (suction condition of a2), −30 kPa (suction condition of a3), −50 kPa (suction condition of a4), and −70 kPa (suction condition of a5) so that the suction levels are changed. Using the same conditions other than the suction condition, the printing step and the measuring step are performed.

FIG. 30 shows the relationship between a suction condition of the print sheet at this stage and the obtained decreasing change rate α. As shown in FIG. 30, as the suction condition of the print sheet D changes from a1 (without suction) to a5 (−70 kPa) to increase the suction force, the decreasing change rate α increases. Since the change in thickness of the print sheet is correlated with cockling, the greater the thickness decreasing change rate α (the smaller the absolute value of α), the greater the effect of cockling reduction. Accordingly, it is assumed that whether or not cockling occurs in, for example, the printed matter of the actual printing in which the maximum ink ejection amount is 28 g/m² depends on the threshold determined in the above-described manner, that is, β=−1. More specifically, in the present example, the suction condition for the threshold β=−1 is a4 in which the suction condition is −50 kPa. Thus, a4 is determined to be the suction condition. As a result, the actual printing is performed such that the time from the end of printing to the release of suction is 10 seconds. As a result, it is possible to obtain a print image in which cockling is appropriately reduced.

With the drying condition thus obtained, the actual printing is performed until the image to be printed or the print sheet is changed. When another actual printing is performed subsequently, it is preferable to determine the threshold β in the same manner to determine the drying condition. However, in a case where the same print sheet is used, for example, the threshold β can be constant, whereas in a case where different images are printed on the same print sheet, it is possible to omit the step of determining the threshold β. In a case where a frequently-used print sheet is used, it is also possible to determine in advance at a plant or the like the threshold β or a drying condition determined based on the threshold β, and store them in memory in advance and use them.

While the present invention has been described with reference to exemplary embodiments, it is to be understood that the invention is not limited to the disclosed exemplary embodiments. The scope of the following claims is to be accorded the broadest interpretation so as to encompass all such modifications and equivalent structures and functions.

This application claims the benefit of Japanese Patent Application No. 2013-118029, filed Jun. 4, 2013, which is hereby incorporated by reference herein in its entirety.

What is claimed is:

1. A printing apparatus comprising:
a holding unit configured to hold a sheet by suction;
a printing unit configured to perform printing by applying ink to the sheet held by the holding unit;
a measuring unit configured to measure a thickness of the sheet to which ink has been applied, wherein the holding unit maintains holding of the sheet while measuring is effected by the measuring unit; and
a determination unit configured to determine an operating condition in printing performed by the printing unit, based on the measured thickness,
wherein the operating condition is at least a timing at which the suction applied to the sheet by the holding unit is released in a case where a thickness change rate with respect to a thickness of the sheet before ink is applied, which decreases with elapsed time after applying ink to the sheet, is less than a threshold.

2. The printing apparatus as claimed in claim 1, wherein the measuring unit measures the thickness by using a laser to measure a distance to a surface of the sheet.

3. The printing apparatus as claimed in claim 2, wherein the measuring unit measures the distance before applying ink and after applying ink to determine the thickness change rate.

4. The printing apparatus as claimed in claim 1, further comprising a performing unit configured to perform an operation of printing an image on the sheet by using the printing unit according to the operating condition determined by the determination unit.

5. A printing method comprising the steps of:
holding a sheet by suction with a holding unit;
measuring a thickness of the sheet to which liquid has been applied, wherein the holding unit maintains holding of the sheet by suction while the sheet is subjected to measurement of the thickness; and
determining an operating condition in printing in which ink is applied to the sheet, based on the measured thickness,
wherein the operating condition is at least a timing at which the suction applied to the sheet by the holding unit is released in a case where a thickness change rate with respect to a thickness of the sheet before ink is applied, which decreases with elapsed time after applying ink to the sheet, is less than a threshold.

6. The printing method as claimed in claim 5, wherein the measuring step measures the thickness by using a laser to measure a distance to a surface of the sheet.

7. The printing method as claimed in claim 6, wherein the measuring step measures the distance before applying ink and after applying ink to determine the thickness change rate.

* * * * *